US012788815B2

(12) United States Patent
Sheen et al.

(10) Patent No.: US 12,788,815 B2
(45) Date of Patent: Nov. 10, 2026

(54) COMPOSITION COMPRISING ANTIGEN-PRESENTING CELL CO-EXPRESSING MHC AND TUMOR ANTIGEN, AND CANCER TREATMENT USING SAME

(71) Applicant: LG CHEM, LTD., Seoul (KR)

(72) Inventors: Joon Ho Sheen, Daejeon (KR); Joon Cheol Kwon, Daejeon (KR); Seunghae Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1099 days.

(21) Appl. No.: 17/791,685

(22) PCT Filed: Jan. 8, 2021

(86) PCT No.: PCT/KR2021/000281

§ 371 (c)(1),
(2) Date: Jul. 8, 2022

(87) PCT Pub. No.: WO2021/141456

PCT Pub. Date: Jul. 15, 2021

(65) Prior Publication Data

US 2023/0338530 A1 Oct. 26, 2023

(30) Foreign Application Priority Data

Jan. 10, 2020 (KR) ........................ 10-2020-0003910
Oct. 14, 2020 (KR) ........................ 10-2020-0133005

(51) Int. Cl.

| | |
|---|---|
| *A61K 40/19* | (2025.01) |
| *A61K 39/00* | (2006.01) |
| *A61K 40/24* | (2025.01) |
| *A61K 40/42* | (2025.01) |
| *A61P 35/00* | (2006.01) |
| *C12N 5/0784* | (2010.01) |

(52) U.S. Cl.

CPC .............. *A61K 40/19* (2025.01); *A61K 40/24* (2025.01); *A61K 40/424* (2025.01); *A61K 40/4268* (2025.01); *A61K 40/4269* (2025.01); *A61K 40/4272* (2025.01); *A61P 35/00* (2018.01); *C12N 5/0639* (2013.01); *A61K 2039/605* (2013.01); *A61K 2239/48* (2023.05)

(58) Field of Classification Search

None

See application file for complete search history.

(56) References Cited

U.S. PATENT DOCUMENTS

| | | | | |
|---|---|---|---|---|
| 2005/0008622 | A1 | 1/2005 | Kang et al. | |
| 2005/0272151 | A1 | 12/2005 | Plumas et al. | |
| 2010/0189728 | A1 | 7/2010 | Schendel et al. | |
| 2012/0020998 | A1 | 1/2012 | Plumas et al. | |
| 2014/0105923 | A1* | 4/2014 | Kim | A61K 40/19 435/325 |
| 2017/0314078 | A1 | 11/2017 | Sahin et al. | |
| 2019/0000949 | A1 | 1/2019 | Milosevic et al. | |
| 2019/0070275 | A1 | 3/2019 | Ethell | |
| 2019/0167722 | A1* | 6/2019 | Soon-Shiong | A61K 40/19 |
| 2019/0241658 | A1* | 8/2019 | Frederick | C07K 16/2818 |
| 2019/0381154 | A1 | 12/2019 | Russell et al. | |

FOREIGN PATENT DOCUMENTS

| | | | | | |
|---|---|---|---|---|---|
| JP | 2002-506633 | A | | 3/2002 | |
| JP | 2003-000242 | A | | 1/2003 | |
| JP | 2011-501758 | A | | 1/2011 | |
| JP | 2014-513948 | A | | 6/2014 | |
| KR | 10-2004-0046804 | A | | 6/2004 | |
| KR | 10-2012-0119538 | A | | 10/2012 | |
| KR | 10-2015-0123175 | A | | 11/2015 | |
| WO | 1999-047641 | A1 | | 9/1999 | |
| WO | 2004-061089 | A1 | | 7/2004 | |
| WO | 2008-057529 | A2 | | 5/2008 | |
| WO | 2009-034172 | A1 | | 3/2009 | |
| WO | 2009-138489 | A1 | | 11/2009 | |
| WO | 2012-145384 | A1 | | 10/2012 | |
| WO | 2012-159643 | A1 | | 11/2012 | |
| WO | 2016-040900 | A1 | | 3/2016 | |
| WO | WO-2018230938 | A1 | * | 12/2018 | A61K 35/17 |
| WO | WO-2019195310 | A1 | * | 10/2019 | G01N 33/56972 |

OTHER PUBLICATIONS

International Search Report issued for International Application No. PCT/KR2021/000281 on Apr. 27, 2021, 8 pages.
Capone, et al., "Fusion of HCV Nonstructural Antigen to MHC Class II—associated Invariant Chain Enhances T-cell Responses Induced by Vectored Vaccines in Nonhuman Primates", Molecular Therapy, 2014, vol. 22, No. 5, 1039-1047.
McDonnell et al., "Tumor Antigen Cross-Presentation and the Dendritic Cell: Where it All Begins?", Clinical and Developmental Immunology, 2010, vol. 2010, Article ID 539519, 1-9.
Ordaz et al., "DC-expressed MHC class I single-chain trimer-based vaccines prime cytotoxic T lymphocytes against exogenous but not endogenous antigens," Cellular Immunology, 2010, vol. 262, pp. 141-149.
Wilde et al., "Dendritic cells pulsed with RNA encoding allogeneic MHC and antigen induce T cells with superior antitumor activity and higher TCR functional avidity," Blood, vol. 114, No. 10, Jul. 8, 2009, pp. 2131-2139.

(Continued)

*Primary Examiner* — Peter Johansen

(74) *Attorney, Agent, or Firm* — ROTHWELL, FIGG, ERNST & MANBECK, P.C.

(57) ABSTRACT

Provided are a vaccine composition for preventing or treating cancer, the vaccine composition comprising antigen-presenting cells, on the cell surface of which a complex of a major histocompatibility complex (MHC) and a tumor antigen is overexpressed, and cancer treatment using the same.

18 Claims, 11 Drawing Sheets

Specification includes a Sequence Listing.

(56) References Cited

OTHER PUBLICATIONS

Extended European Search Report issued for European Patent Application No. 21738954.3 on Jun. 21, 2023, 7 pages.

* cited by examiner

【FIG. 1】
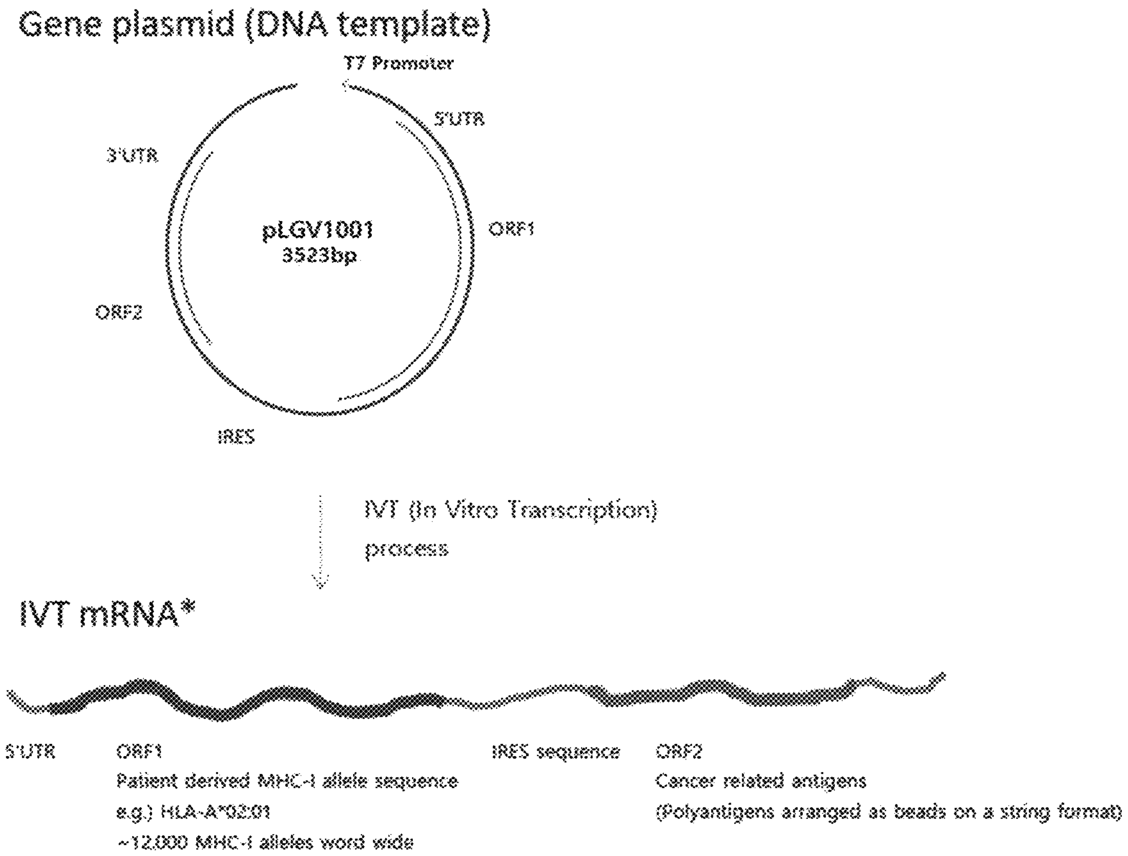

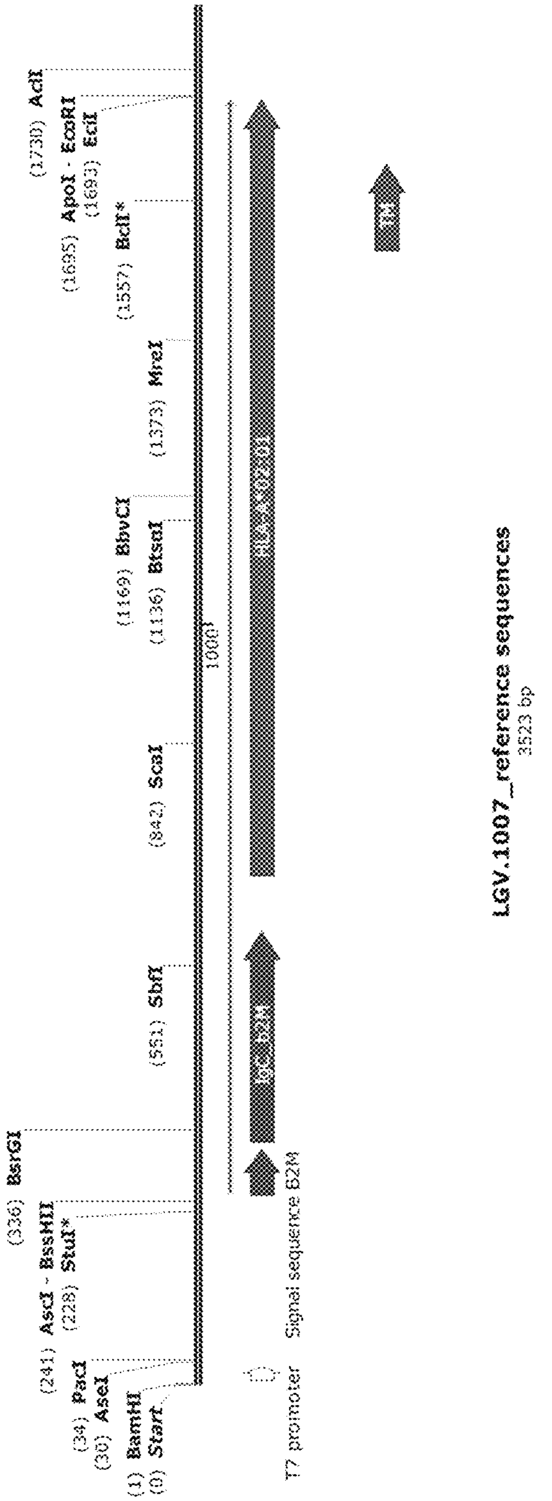
[FIG. 2A]

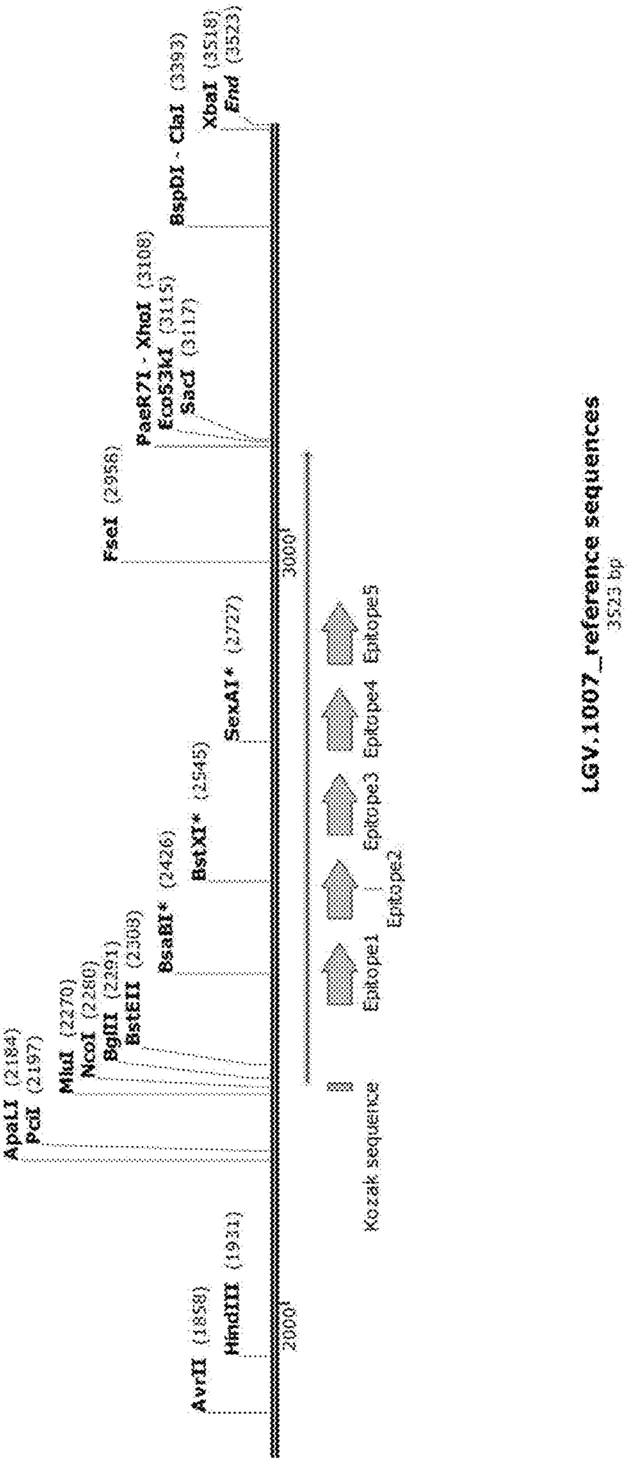
【FIG. 2B】

【FIG. 3】
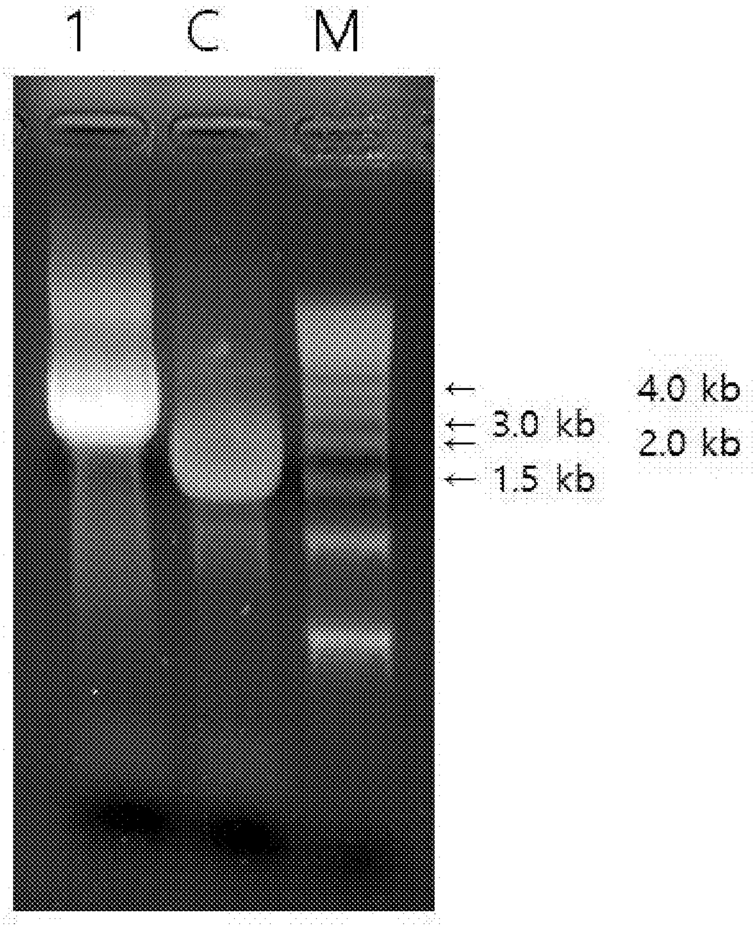
*In vitro* transcription for mRNA production
Lane 1 : LGV1007 (3.5 kb)
C : IVT control (pTRI-Xef 1.85 kb Xenopus EF1α)
M : RNA Size Marker 【FIG. 4A】
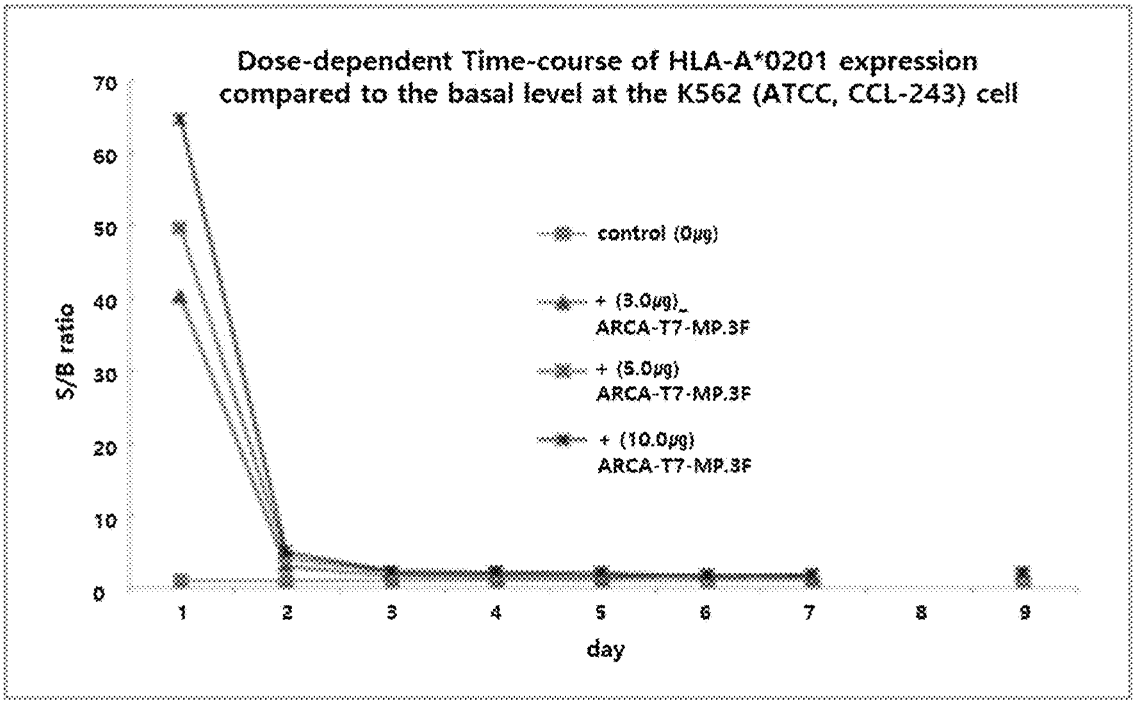
【FIG. 4B】
| | B01(0ug) | B02 (3ug) | B03(5ug) | B04(10ug) |
|---|---|---|---|---|
| The values of the S/B ratio | | | | |
| Day | control (0μg) | + (3.0μg)_ ARCA-T7-MP3F | + (5.0μg)_ ARCA-T7-MP3F | + (10.0μg)_ ARCA-T7-MP3F |
| 1 | 1 | 40.2 | 49.6 | 64.6 |
| 2 | 1 | 3.0 | 4.1 | 4.9 |
| 3 | 1 | 1.7 | 2.1 | 2.3 |
| 4 | 1 | 1.6 | 1.9 | 2.2 |
| 5 | 1 | 1.5 | 1.9 | 2.0 |
| 6 | 1 | 1.7 | 1.6 | 1.7 |
| 7 | 1 | 1.5 | 1.8 | 1.8 |
| 8 | | | | |
| 9 | 1 | 1.6 | 1.7 | 2.1 |
S/B ratio : calculated from the ratio based on the Median Fluorescence Intensity
S: Signal Intensity (MFI) B: Background MFI of control (Basal level)

【FIG. 4C】
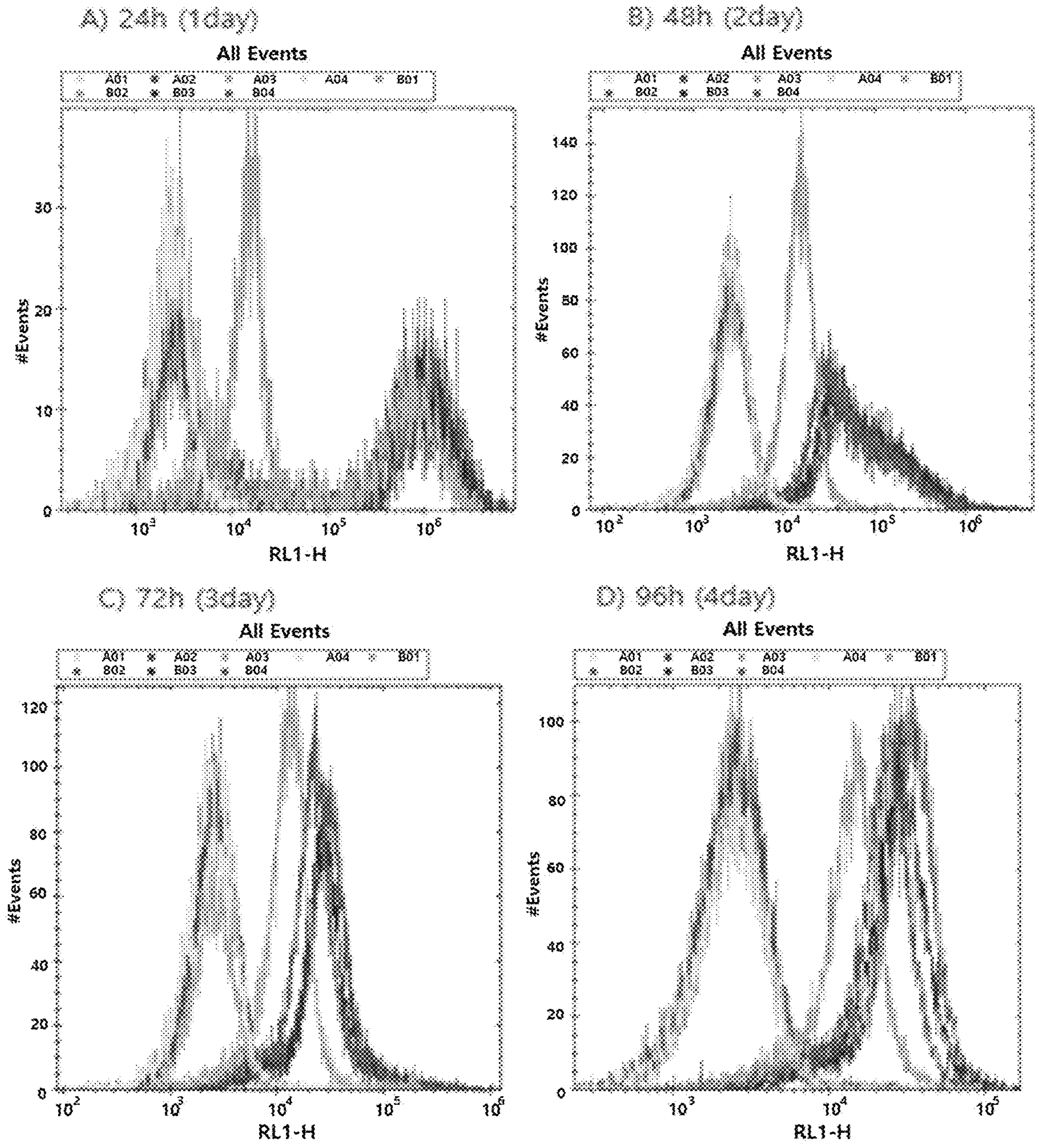

【FIG. 5】
- LGV1007 mRNA mediated polyantigen (pentatope fusion protein) generation in vitro translation system
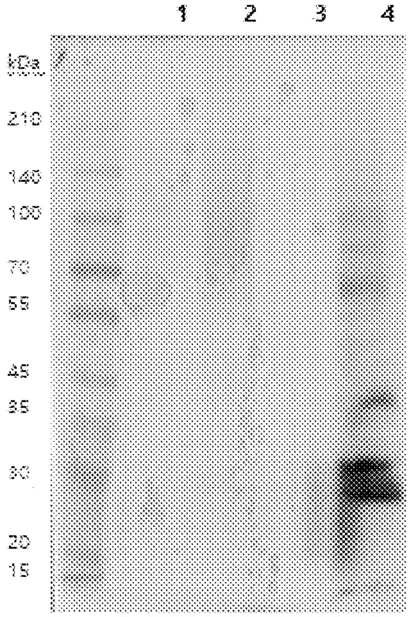
1: (-)
2: T7-MP.3F plasmid DNA
3. (-)
4. T7-MP.3F plasmid DNA
1–2: TnT T7 Quick Coupled Transcription/Translation System
3–4: 1-Step High Yield Mini IVT Kit (Thermo)

【FIG. 6A】
**LGV1007 mRNA mediated HLA-A*0201 expression in K562 cells**
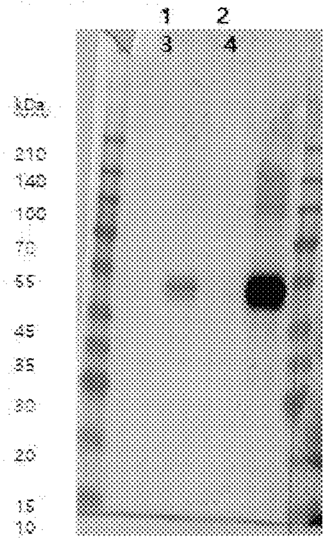
1: K562 control
2: T7-MP transfected K562
3. T7-PM transfected K562
4. ARCA-T7-MP.3F electroporated K562
- Expected molecular weight:
✓ HLA-A*0201: ~51kDa
【FIG. 6B】
LGV1007 mRNA mediated polyantigen expression in K562 cells
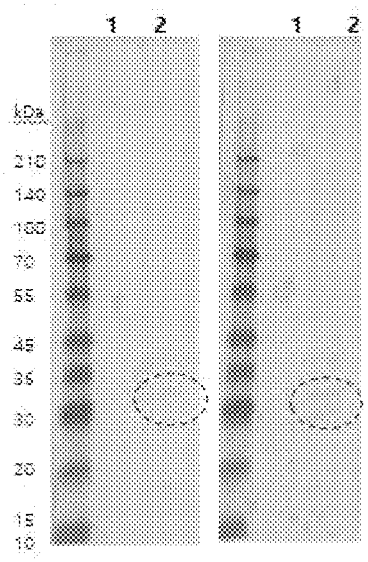
1: : K562 control
2: ARCA-T7-MP.3F electroporated K562
IVT_T7-MP.3F-A118−3xFlag_Pentatope
- Expected Molecular Weight:
1) 3x flag-pentatope : 299 a.a = ~ 30kDa 【FIG. 7】
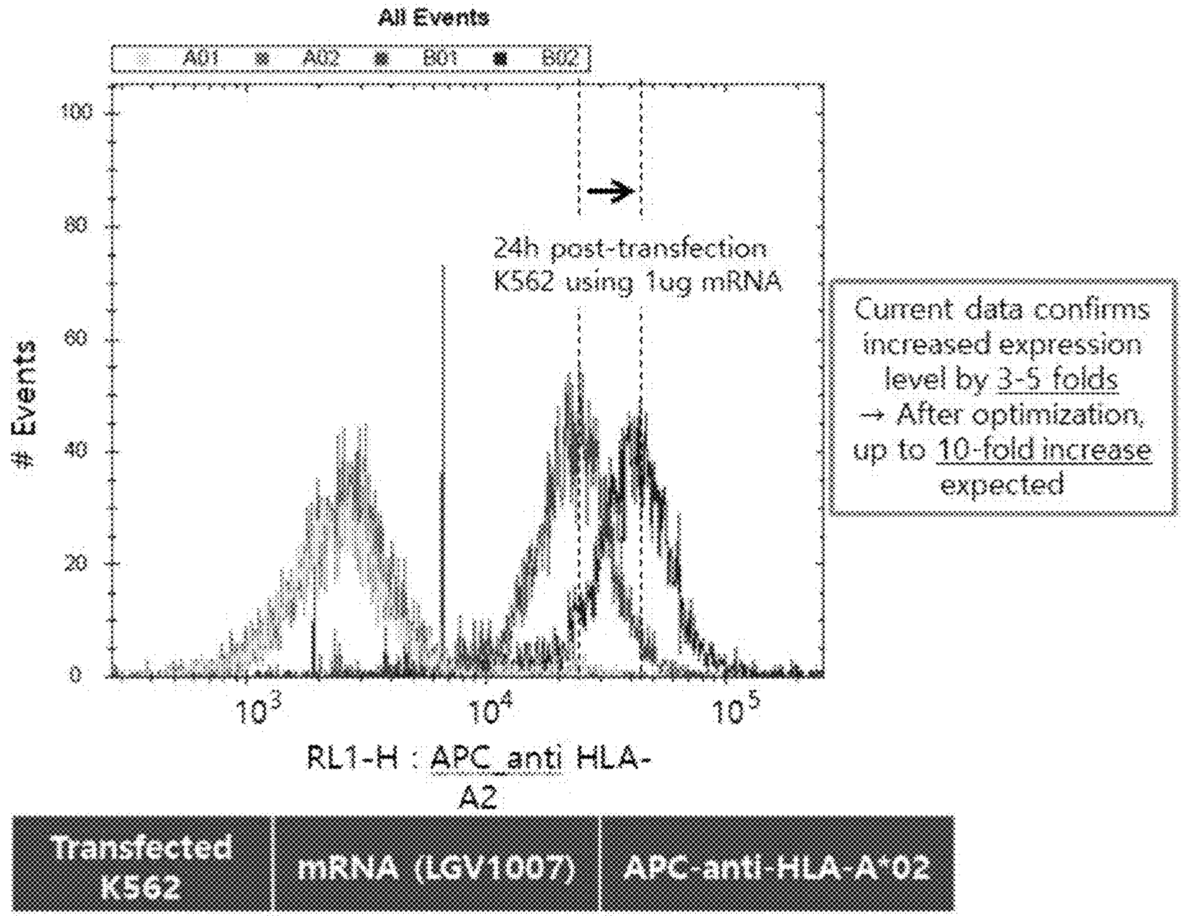
| Transfected K562 | mRNA (LGV1007) | APC-anti-HLA-A*02 |
|---|---|---|
| A01 | - | - |
| A02 | + | - |
| B01 | - | + |
| B02 | + | + |

【FIG. 8】
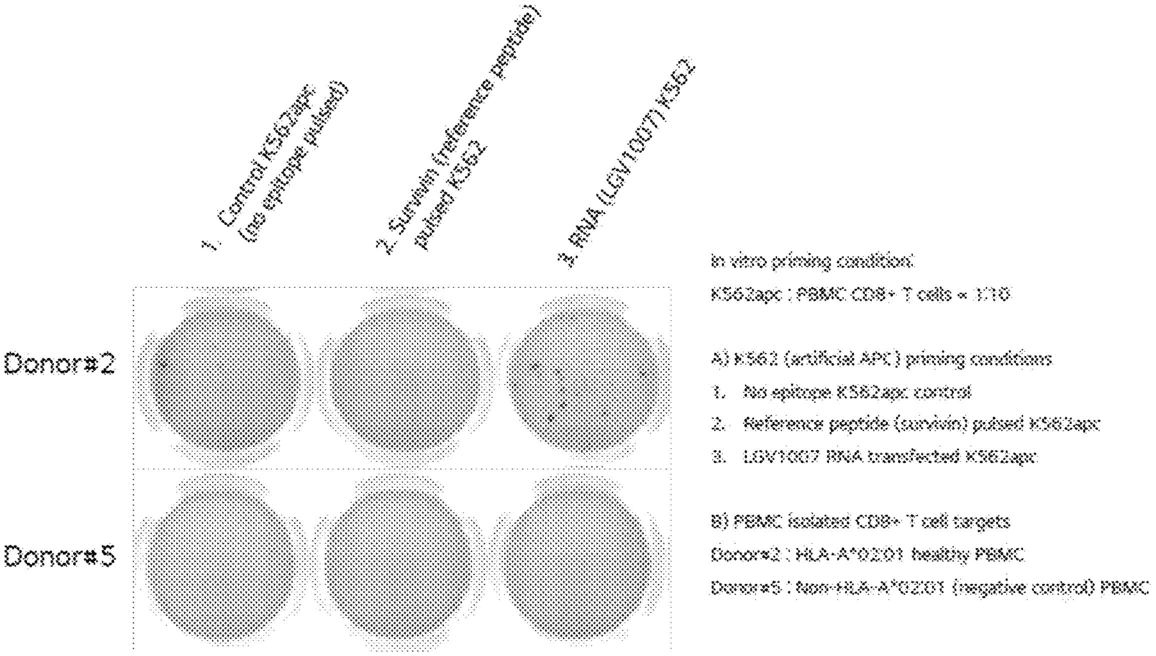
【FIG. 9】
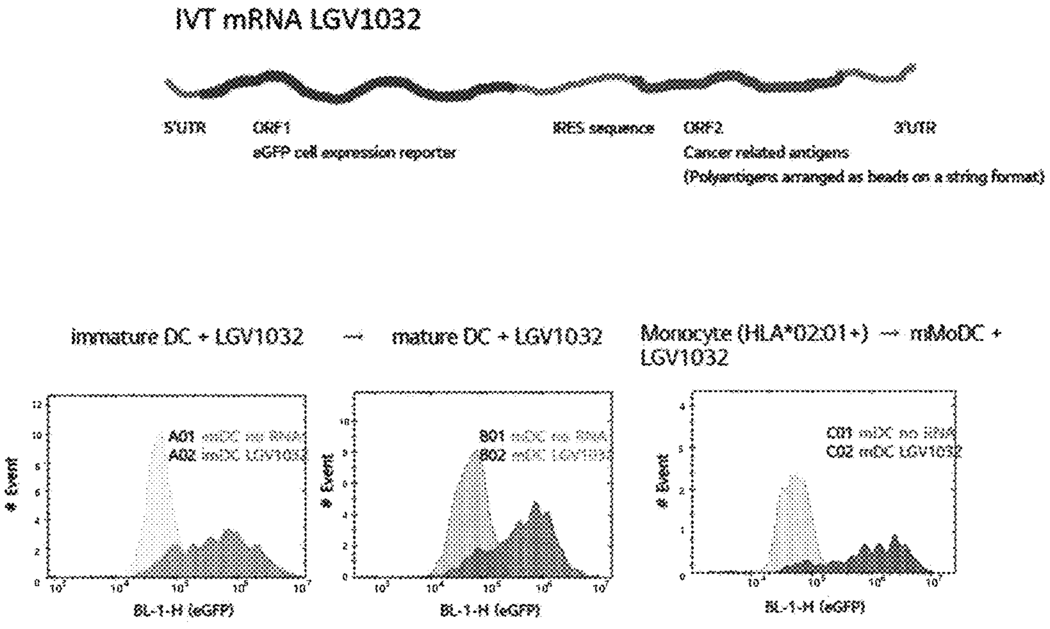
FACS analysis of RNA introduction and expression in MoDC 【FIG. 10】
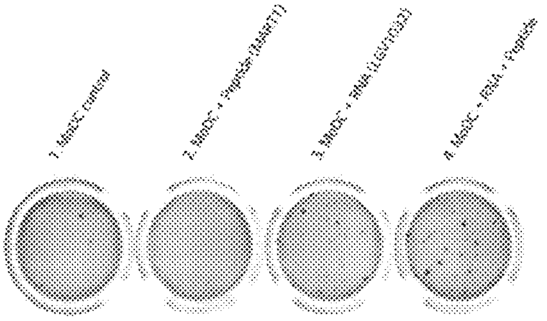
ELISPOT IFNγ assay using anti-MART1 TCRe T cells (HLA-A*02:01)
1. MoDC only (no epitope pulsed) control
2. MoDC pulsed with reference peptide (MART1)
3. MoDC transfected with LGV1007 RNA
4. MoDC with RNA LGV1007 + MART1 peptide
Antigen immune assay using Anti-MART1 TCRe T cell (Astarte)
Donor 358 (HLA-A*02:01)
CD8+ 100%,
MART1+ 95.6%

SEQUENCE LISTING

```
<160> NUMBER OF SEQ ID NOS: 3

<210> SEQ ID NO 1
<211> LENGTH: 480
<212> TYPE: PRT
<213> ORGANISM: Artificial Sequence
<220> FEATURE:
<223> OTHER INFORMATION: ORF1 (Signal sequence - B2M - HLA-A*02:01 MHC-I
      protein)

<400> SEQUENCE: 1

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Gly Gly Gly Gly Ser Gly Gly Gly Gly
        115                 120                 125

Ser Gly Gly Gly Gly Ser Gly Gly Gly Gly Ser Gly Ser His Ser Met
    130                 135                 140

Arg Tyr Phe Phe Thr Ser Val Ser Arg Pro Gly Arg Gly Glu Pro Arg
145                 150                 155                 160

Phe Ile Ala Val Gly Tyr Val Asp Asp Thr Gln Phe Val Arg Phe Asp
                165                 170                 175

Ser Asp Ala Ala Ser Gln Arg Met Glu Pro Arg Ala Pro Trp Ile Glu
            180                 185                 190

Gln Glu Gly Pro Glu Tyr Trp Asp Gly Glu Thr Arg Lys Val Lys Ala
```

```
        195                 200                 205

His Ser Gln Thr His Arg Val Asp Leu Gly Thr Leu Arg Gly Tyr Tyr
    210                 215                 220

Asn Gln Ser Glu Ala Gly Ser His Thr Val Gln Arg Met Tyr Gly Cys
225                 230                 235                 240

Asp Val Gly Ser Asp Trp Arg Phe Leu Arg Gly Tyr His Gln Tyr Ala
                245                 250                 255

Tyr Asp Gly Lys Asp Tyr Ile Ala Leu Lys Glu Asp Leu Arg Ser Trp
            260                 265                 270

Thr Ala Ala Asp Met Ala Ala Gln Thr Thr Lys His Lys Trp Glu Ala
        275                 280                 285

Ala His Val Ala Glu Gln Trp Arg Ala Tyr Leu Glu Gly Thr Cys Val
    290                 295                 300

Glu Trp Leu Arg Arg Tyr Leu Glu Asn Gly Lys Glu Thr Leu Gln Arg
305                 310                 315                 320

Thr Asp Ala Pro Lys Thr His Met Thr His His Ala Val Ser Asp His
                325                 330                 335

Glu Ala Thr Leu Arg Cys Trp Ala Leu Ser Phe Tyr Pro Ala Glu Ile
            340                 345                 350

Thr Leu Thr Trp Gln Arg Asp Gly Glu Asp Gln Thr Gln Asp Thr Glu
        355                 360                 365

Leu Val Glu Thr Arg Pro Ala Gly Asp Gly Thr Phe Gln Lys Trp Ala
    370                 375                 380

Ala Val Val Val Pro Ser Gly Gln Glu Gln Arg Tyr Thr Cys His Val
385                 390                 395                 400

Gln His Glu Gly Leu Pro Lys Pro Leu Thr Leu Arg Trp Glu Pro Ser
                405                 410                 415

Ser Gln Pro Thr Ile Pro Ile Val Gly Ile Ile Ala Gly Leu Val Leu
            420                 425                 430

Phe Gly Ala Val Ile Thr Gly Ala Val Val Ala Ala Val Met Trp Arg
        435                 440                 445

Arg Lys Ser Ser Asp Arg Lys Gly Gly Ser Tyr Ser Gln Ala Ala Ser
    450                 455                 460

Ser Asp Ser Ala Gln Gly Ser Asp Val Ser Leu Thr Ala Cys Lys Val
465                 470                 475                 480


<210> SEQ ID NO 2
<211> LENGTH: 274
<212> TYPE: PRT
<213> ORGANISM: Artificial Sequence
<220> FEATURE:
<223> OTHER INFORMATION: ORF2 (NY-ESO1 - GS linker - MAGE-A3 - GS
      linker - SURVIVIN - GS linker - MULTI-MAGE-A - GS linker - MELAN-A
      epitope)

<400> SEQUENCE: 2

Met Ala Thr Arg Ser Ala Thr Met Arg Val Thr Ala Pro Arg Thr Leu
1               5                   10                  15

Ile Leu Leu Leu Ser Gly Ala Leu Ala Leu Thr Glu Thr Trp Ala Gly
            20                  25                  30

Ser Leu Gln Ser Ile Ser Ser Cys Leu Gln Gln Leu Ser Leu Leu Met
        35                  40                  45

Trp Ile Thr Gln Cys Phe Leu Pro Val Phe Leu Ala Gln Pro Gly Gly
    50                  55                  60

Ser Gly Gly Gly Gly Ser Gly Gly Pro Gly Ser Asp Pro Ala Cys Tyr
65                  70                  75                  80
```

Glu Phe Leu Trp Gly Pro Arg Ala Leu Val Glu Thr Ser Tyr Val Lys
85 90 95

Val Leu Gly Gly Ser Gly Gly Gly Gly Ser Gly Gly Leu Ser Val Lys
100 105 110

Lys Gln Phe Glu Glu Leu Met Leu Gly Glu Phe Leu Lys Leu Asp Arg
115 120 125

Glu Arg Ala Lys Asn Lys Ile Gly Gly Ser Gly Gly Gly Gly Ser Gly
130 135 140

Gly Leu Thr Gln Asp Leu Val Gln Glu Lys Tyr Leu Glu Tyr Arg Gln
145 150 155 160

Val Pro Val Ser Asp Pro Ala Arg Tyr Glu Phe Leu Gly Gly Ser Gly
165 170 175

Gly Gly Gly Ser Gly Gly His Gly His Ser Tyr Thr Thr Ala Glu Glu
180 185 190

Leu Ala Gly Ile Gly Ile Leu Thr Val Ile Leu Gly Val Leu Leu Leu
195 200 205

Ile Gly Gly Ser Leu Gly Gly Gly Gly Ser Gly Ile Val Gly Ile Val
210 215 220

Ala Gly Leu Ala Val Leu Ala Val Val Val Ile Gly Ala Val Val Ala
225 230 235 240

Thr Val Met Cys Arg Arg Lys Ser Ser Gly Gly Lys Gly Gly Ser Tyr
245 250 255

Ser Gln Ala Ala Ser Ser Asp Ser Ala Gln Gly Ser Asp Val Ser Leu
260 265 270

Thr Ala

<210> SEQ ID NO 3
<211> LENGTH: 3523
<212> TYPE: DNA
<213> ORGANISM: Artificial Sequence
<220> FEATURE:
<223> OTHER INFORMATION: DNA sequence of LGV1007 (HLA-A*02:01 + Polyantigen fusion protein)

<400> SEQUENCE: 3
ggatcctaat acgactcact atagggagat taattaaccg gcgggtttct gacatccggc 60
gggtttctga catccggcgg gtttctgaca tccggcgggt ttctgacatc cggcgggttt 120
ctgacatccg gcgggtttct gacatccggc gggtttctga catccggcgg gtttctgaca 180
tccggcgggt ttctgacatc cggcgggttt ctgacattca caaccaggcc tccacaaccg 240
gcgcgccacc atgagcagga gcgtggccct ggccgtgctg gccctgctga gcctgagcgg 300
cctggaggcc atccagagga cccccaagat ccaggtgtac agcaggcacc ccgccgagaa 360
cggcaagagc aacttcctga actgctacgt gagcggcttc caccccagcg acatcgaggt 420
ggacctgctg aagaacggcg agaggatcga gaaggtggag cacagcgacc tgagcttcag 480
caaggactgg agcttctacc tgctgtacta caccgagttc acccccaccg agaaggacga 540
gtacgcctgc agggtgaacc acgtgaccct gagccagccc aagatcgtga agtgggacag 600
ggacatgggc ggcggcggca gcggcggcgg cggcagcggc ggcggcggca gcggcggcgg 660
cggcagcggc agccacagca tgaggtactt cttcaccagc gtgagcaggc ccggcagggg 720
cgagcccagg ttcatcgccg tgggctacgt ggacgacacc cagttcgtga ggttcgacag 780
cgacgccgcc agccagagga tggagcccag ggcccccctgg atcgagcagg agggccccga 840
gtactgggac ggcgagacca ggaaggtgaa ggcccacagc cagacccaca gggtggacct 900

```
gggcaccctg aggggctact acaaccagag cgaggccggc agccacaccg tgcagaggat    960
gtacggctgc gacgtgggca gcgactggag gttcctgagg ggctaccacc agtacgccta   1020
cgacggcaag gactacatcg ccctgaagga ggacctgagg agctggaccg ccgccgacat   1080
ggccgcccag accaccaagc acaagtggga ggccgcccac gtggccgagc agtggagggc   1140
ctacctggag ggcacctgcg tggagtggct gaggaggtac ctggagaacg gcaaggagac   1200
cctgcagagg accgacgccc ccaagaccca catgacccac cacgccgtga gcgaccacga   1260
ggccaccctg aggtgctggg ccctgagctt ctaccccgcc gagatcaccc tgacctggca   1320
gagggacggc gaggaccaga cccaggacac cgagctggtg gagaccaggc ccgccggcga   1380
cggcaccttc cagaagtggg ccgccgtggt ggtgcccagc ggccaggagc agaggtacac   1440
ctgccacgtg cagcacgagg gcctgcccaa gcccctgacc ctgaggtggg agcccagcag   1500
ccagcccacc atccccatcg tgggcatcat cgccggcctg gtgctgttcg gcgccgtgat   1560
caccggcgcc gtggtggccg ccgtgatgtg gaggaggaag agcagcgaca ggaagggcgg   1620
cagctacagc caggccgcca gcagcgacag cgcccagggc agcgacgtga gcctgaccgc   1680
ctgcaaggtg taaagaattc attccgcccc tctccctccc ccccccctaa cgttactggc   1740
cgaagccgct tggaataagg ccggtgtgcg tttgtctata tgttattttc caccatattg   1800
ccgtcttttg gcaatgtgag ggcccggaaa cctggccctg tcttcttgac gagcattcct   1860
aggggtcttt cccctctcgc caaaggaatg caaggtctgt tgaatgtcgt gaaggaagca   1920
gttcctctgg aagcttcttg aagacaaaca acgtctgtag cgaccctttg caggcagcgg   1980
aacccccac ctggcgacag gtgcctctgc ggccaaaagc cacgtgtata agatacacct   2040
gcaaaggcgg cacaacccca gtgccacgtt gtgagttgga tagttgtgga aagagtcaaa   2100
tggctctcct caagcgtatt caacaagggg ctgaaggatg cccagaaggt accccattgt   2160
atgggatctg atctggggcc tcggtgcaca tgctttacat gtgtttagtc gaggttaaaa   2220
aacgtctagg ccccccgaac cacggggacg tggttttcct ttgaaaaaca cgcgtgccac   2280
catggccaca agatctgcca ccatgagggt gaccgccccc aggaccctga tcctgctgct   2340
gagcggcgcc ctggccctga ccgagacctg ggccggcagc ctgcagagca tcagcagctg   2400
cctgcagcag ctgagcctgc tgatgtggat cacccagtgc ttcctgcccg tgttcctggc   2460
ccagcccggc ggcagcggcg gcggcggcag cggcggcccc ggcagcgacc ccgcctgcta   2520
cgagttcctg tggggcccca gggccctggt ggagaccagc tacgtgaagg tgctgggcgg   2580
cagcggcggc ggcggcagcg gcggcctgag cgtgaagaag cagttcgagg agctgatgct   2640
gggcgagttc ctgaagctgg acagggagag ggccaagaac aagatcggcg gcagcggcgg   2700
cggcggcagc ggcggcctga cccaggacct ggtgcaggag aagtacctgg agtacaggca   2760
ggtgcccgtg agcgaccccg ccaggtacga gttcctgggc ggcagcggcg gcggcggcag   2820
cggcggccac ggccacagct acaccaccgc cgaggagctg gccggcatcg gcatcctgac   2880
cgtgatcctg ggcgtgctgc tgctgatcgg cggcagcctg ggcggcggcg gcagcggcat   2940
cgtgggcatc gtggccggcc tggccgtgct ggccgtggtg gtgatcggcg ccgtggtggc   3000
caccgtgatg tgcaggagga agagcagcgg cggcaagggc ggcagctaca gccaggccgc   3060
cagcagcgac agcgcccagg gcagcgacgt gagcctgacc gcctaaactc gagagctcgc   3120
tttcttgctg tccaatttct attaaaggtt cctttgttcc ctaagtccaa ctactaaact   3180
gggggatatt atgaagggcc ttgagcatct ggattctgcc taataaaaaa catttatttt   3240
```

-continued

```
cattgctgcg gatctagctc gctttcttgc tgtccaattt ctattaaagg ttcctttgtt   3300

ccctaagtcc aactactaaa ctgggggata ttatgaaggg ccttgagcat ctggattctg   3360

cctaataaaa aacatttatt ttcattgctg catcgataaa aaaaaaaaaa aaaaaaaaaa   3420

aaaaaaaaaa aaaaaaaaaa aaaaaaaaaa aaaaaaaaaa aaaaaaaaaa aaaaaaaaaa   3480

aaaaaaaaaa aaaaaaaaaa aaaaaaaaaa aaaaaaatct aga                     3523
```

COMPOSITION COMPRISING ANTIGEN-PRESENTING CELL CO-EXPRESSING MHC AND TUMOR ANTIGEN, AND CANCER TREATMENT USING SAME

TECHNICAL FIELD

Cross-Reference to Related Application

The application is a 35 U.S.C. 371 National Phase Entry Application from PCT/KR2021/000281 filed on Jan. 8, 2021, which claims priority from, Korean Patent Application Nos. 10-2020-0003910 and 10-2020-0133005, filed on Jan. 10, 2020 and Oct. 14, 2020, respectively, the disclosures of which are hereby incorporated by reference herein in their entirety.

The present application includes a Sequence Listing filed in electronic format. The Sequence Listing is entitled "KR2021000281-SEQ_ST25.txt" created on Jul. 8, 2022 and is 11976 bytes in size. The information in the electronic format of the Sequence Listing is part of the present application and is incorporated herein by reference in its entirety.

The present invention relates to a vaccine composition for preventing or treating cancer, the vaccine composition comprising antigen-presenting cells, on the cell surface of which a complex of a major histocompatibility complex (MHC) and a tumor antigen is overexpressed, and cancer treatment using the same.

BACKGROUND OF THE INVENTION

An anticancer therapeutic cell vaccine is expected to fulfill its role as an anticancer vaccine when administered to cancer patients by loading tumor antigens onto specialized antigen-presenting cells, for example, dendritic cells.

However, an epitope peptide incubation method commonly used for antigen loading inevitably has restrictions in the range of antigen-presenting epitope sequences and the overall antigen presentation efficacy by a specific MHC allele already expressed in cells and its expression level according to a mechanism based on epitope-MHC restriction of the specific MHC allele of the antigen-presenting cells and the antigen epitope.

BRIEF SUMMARY OF THE INVENTION

In order to apply tumor antigens, in particular, various patient-specific neoantigens derived from individual cancer patients with different cell-specific MHCs in anticancer cell vaccines standardized for therapeutic purposes, it is ultimately required to develop a new technology for producing a cell vaccine that overcomes the MHC restriction of individual antigen-presenting cells, and accordingly, it is intended to solve this problem.

In one aspect, there is provided a vaccine composition for preventing or treating cancer, the vaccine composition comprising antigen-presenting cells, on the cell surface of which a complex of a major histocompatibility complex (MHC) and a tumor antigen is overexpressed.

In another aspect, there is provided a method of treating cancer, the method comprising the step of administering, to a patient, the antigen-presenting cells, on the cell surface of which the complex of the MHC and the tumor antigen is overexpressed.

In still another aspect, there is provided antigen-presenting cells used for cancer treatment, the antigen-presenting cells on the cell surface of which the complex of the MHC and the tumor antigen is overexpressed.

In still another aspect, there is provided use of the antigen-presenting cells in the preparation of therapeutic agents for cancer, the antigen-presenting cells on the cell surface of which the complex of the MHC and the tumor antigen is overexpressed.

In still another aspect, there is provided a method of preparing a vaccine composition for preventing or treating cancer, the method comprising the step of introducing, into antigen-presenting cells, a gene construct co-expressing the MHC allele and the tumor antigen gene; an expression vector comprising the gene construct; an RNA transcript transcribed from the gene construct; or a polypeptide produced from the gene construct, expression vector, or RNA transcript.

The present invention is based on the idea that the "restrictions in the antigen presenting ability by a specific MHC allele and reference cell expression level" are solved even in standardized specific antigen-presenting cells by using a bicistronic gene construct or mRNA transcript co-expressing a patient's tumor-derived cell-specific MHC allele and a tumor antigen at the maximum amount.

In particular, in the present invention, a tumor-derived neoantigen sequence obtained from a patient tumor analysis and a tumor-derived MHC allele of each patient are simultaneously overexpressed in antigen-presenting cells, and the maximum amount of an "epitope-MHC immunostimulatory complex" is expressed on the cell surface to maximize the tumor antigen presentation efficacy of the antigen-presenting cells, and the complex is administered to the patient, ultimately leading to promoting proliferation and activation of patient-specific anticancer T cells and maximizing the neoantigen-specific anticancer immune effect.

According to an aspect of the present invention, there is provided a vaccine composition for preventing or treating cancer, the vaccine composition comprising antigen-presenting cells, on the cell surface of which a complex of a major histocompatibility complex (MHC) and a tumor antigen is overexpressed.

There is also provided a method of treating cancer, the method comprising the step of administering, to a patient, the antigen-presenting cells, on the cell surface of which the complex of the MHC and the tumor antigen is overexpressed.

There is also provided antigen-presenting cells used for cancer treatment, on the cell surface of which the complex of the MHC and the tumor antigen is overexpressed.

There is also provided use of the antigen-presenting cells in the preparation of therapeutic agents for cancer, the antigen-presenting cells, on the cell surface of which the complex of the MHC and the tumor antigen is overexpressed.

In an embodiment, the antigen-presenting cells may be dendritic cells.

In an embodiment, the antigen-presenting cells may comprise a gene construct co-expressing the MHC allele and the tumor antigen gene; an expression vector comprising the gene construct; or an RNA transcript transcribed from the gene construct, the RNA transcript co-expressing the MHC allele and the tumor antigen gene; or a polypeptide produced from the gene construct, expression vector, or RNA transcript, thereby overexpressing the complex of the MHC and the tumor antigen on the cell surface.

In an embodiment, the MHC may be an MHC class I or an MHC class II.

In an embodiment, the gene construct may comprise a nucleic acid sequence of the MHC allele and a nucleic acid sequence encoding the tumor antigen.

In an embodiment, the nucleic acid sequence of the MHC allele may be fused with a sequence encoding beta-2-microglobulin (B2M) at the N-terminus thereof.

In an embodiment, the MHC allele and the tumor antigen may be derived from tumor cells of a cancer patient to be treated.

In an embodiment, the tumor antigen may comprise a tumor-associated antigen (TAA), a tumor-specific antigen (TSA), or a tumor-derived neoantigen.

In an embodiment, the tumor-derived neoantigen may comprise a mutation specifically expressed in cancer cells.

In an embodiment, the tumor-associated antigen (TAA) may be gp100, Melan-A/MART, MAGE-A, melanoma antigen E (MAGE), MAGE-3, MAGE-4, MAGE-A3, tyrosinase, TRP2, NY-ESO-1, carcinoembryonic antigen (CEA), PSA, p53, mammaglobin-A, survivin, Muc1 (mucin1)/DF3, metallopanstimulin-1 (MPS-1), cytochrome P450 isoform 1B1, 90K/Mac-2 binding protein, Ep-CAM (MK-1), HSP-70, hTERT (TRT), LEA, LAGE-1/CAMEL, TAGE-1, GAGE, 5T4, gp70, SCP-1, c-myc, cyclin B1, MDM2, p62, Koc, IMP1, RCAS1, TA90, OA1, CT-7, HOM-MEL-40/SSX-2, SSX-1, SSX-4, HOM-TES-14/SCP-1, HOM-TES-85, HDAC5, MBD2, TRIP4, NY-CO-45, KNSL6, HIP1R, Seb4D, KIAA1416, IMP1, 90K/Mac-2 binding protein, MDM2, NY-ESO-1, or LMNA.

In an embodiment, the gene construct may comprise (a) a promoter, 5'-UTR, the nucleic acid sequence of the MHC allele, a nucleic acid sequence of an internal ribosome entry site (IRES), the nucleic acid sequence encoding the tumor antigen, and 3'-UTR in the 5' to 3' direction, or (b) a promoter, 5'-UTR, the nucleic acid sequence encoding the tumor antigen, the nucleic acid sequence of an internal ribosome entry site (IRES), the nucleic acid sequence of the MHC allele, and 3'-UTR in the 5' to 3' direction. In a preferred embodiment, the nucleic acid sequence of the MHC allele may be fused with a sequence encoding beta-2-microglobulin (B2M) at the N-terminus thereof.

In an embodiment, the RNA transcript may be an mRNA transcript.

In an embodiment, the expression vector may be a bicistronic expression vector.

In an embodiment, the gene construct, expression vector, RNA transcript, or polypeptide may be introduced into antigen-presenting cells by electroporation.

In an embodiment, the antigen-presenting cells may be autologous or allogeneic antigen-presenting cells of a cancer patient.

In an embodiment, the vaccine may be a personalized anticancer vaccine.

According to another aspect of the present invention, there is provided a method of preparing the vaccine composition for preventing or treating cancer, the method comprising the step of introducing, into antigen-presenting cells, the gene construct co-expressing the MHC allele and the tumor antigen gene; the expression vector comprising the gene construct; the RNA transcript transcribed from the gene construct; or the polypeptide produced from the gene construct, expression vector, or RNA transcript.

BRIEF DESCRIPTION OF DRAWINGS

FIG. 1 shows configurations of a gene construct co-expressing an MHC class I allele (ORF1) and a tumor antigen (ORF2), and an mRNA transcript in-vitro transcribed therefrom according to one embodiment of the present disclosure;

FIGS. 2A and 2B together show the entire sequence structure of a reference template "LGV1007" according to one embodiment of the present disclosure;

FIG. 3 shows electrophoresis results of confirming production of an mRNA transcript resulting from in-vitro transcription of the reference template "LGV1007" according to one embodiment of the present disclosure;

FIGS. 4A, 4B and 4C show results of examining expression levels of HLA-A*0201 molecules for 9 days after electroporation of K562 cells with the LGV1007 mRNA transcript in an amount of 0 μg, 3 μg, 5 μg, or 10 μg per $1\times10^6$ cells in order to derive conditions under which the expression levels reach the maximum level after electroporation of K562 cells with the LGV1007 mRNA transcript according to one embodiment of the present disclosure;

FIG. 5 shows results of Western blotting for confirming protein expression from the tumor antigen after in-vitro translation of the LGV1007 mRNA transcript according to one embodiment of the present disclosure;

FIG. 6A shows results of Western blotting for confirming protein expression from MHC class I allele (ORF1) after electroporation of K562 cells with the LGV1007 mRNA transcript according to one embodiment of the present disclosure, and FIG. 6B shows results of Western blotting for confirming complete protein expression from the tumor antigen (ORF2);

FIG. 7 shows results of flow cytometry for confirming expression levels of the LGV1007 mRNA transcript on the surface of K562 cells at 24 hours after electroporation of the K562 cells with the LGV1007 mRNA transcript;

FIG. 8 shows results of an ELISPOT IFNγ release assay for measuring the immune activity of PBMC T cells by K562 antigen-presenting cells electroporated with the LGV1007 mRNA transcript;

FIG. 9 shows an illustration of a configuration of the LGV1032 mRNA transcript and results of cell expression in personalized monocyte-derived dendritic cells (MoDCs), in which LGV1032 has a bicistronic transcript configuration homogeneous with that of LGV1007, maintains ORF2 (tumor antigen part), and has a GFP reporter protein as a cell expression marker positioned in ORF1, and LGV1032 was effectively expressed even in individual-derived autologous dendritic cells after electroporation into the cells, like LGV1007; and FIG. 10 shows results of an ELISPOT IFNγ release assay, the results showing that LGV1032 electroporated into individual-derived autologous dendritic cells promotes antigen-specific T cell immune activity through effective antigen presentation.

DETAILED DESCRIPTION OF THE INVENTION

Hereinafter, the present invention will be described in more detail.

An embodiment of the present disclosure relates to a nucleic acid molecule co-expressing an MHC and a tumor antigen.

Further, an embodiment of the present disclosure relates to a nucleic acid composition co-expressing the MHC and the tumor antigen.

Further, an embodiment of the present disclosure relates to a gene construct co-expressing the MHC and the tumor antigen.

Further, an embodiment of the present disclosure relates to an RNA transcript transcribed from the gene construct co-expressing the MHC and the tumor antigen.

Further, an embodiment of the present disclosure relates to antigen-presenting cells, on the cell surface of which a complex of the MHC and the tumor antigen is overexpressed; and a vaccine composition for preventing or treating cancer, the vaccine composition comprising the antigen-presenting cells.

The term "nucleic acid", "nucleic acid molecule", or "nucleic acid sequence" refers to a DNA or RNA molecule or sequence, and the "nucleic acid composition" refers to a composition comprising the nucleic acid, the nucleic acid molecule, or the nucleic acid sequence.

The term "gene construct" refers to a nucleic acid construct operably linked to express a gene insert encoding a target protein. In one embodiment, the gene construct may be a linear or circular, single-stranded or double stranded DNA, cDNA, or RNA encoding two or more target proteins as a bicistronic transcript. The gene construct may form a part of a vector which may be used to transform or transfect a host, but is not limited thereto, and the gene construct itself may be transcribed and/or translated in vitro.

The term "operably linked" refers to a functional linkage between nucleic acid sequences. For example, a coding sequence (e.g., a sequence encoding a target protein) may be operably linked to appropriate control elements to allow replication, transcription, and/or translation thereof. For example, the coding sequence is operably linked to a promoter when the promoter directs transcription of the coding sequence. The control elements need not be contiguous with the coding sequence, as long as they function correctly. For example, intervening untranslated yet transcribed sequences may be present between the promoter sequence and the coding sequence, and the promoter may still be considered "operably linked" to the coding sequence.

Respective components in the gene construct must be operably linked to each other, and linkage of these component sequences may be performed by ligation at a convenient restriction enzyme site, and when such a site does not exist, the ligation may be performed using a synthetic oligonucleotide adapter or linker according to a common method.

The term "bicistronic" or the term "polycistronic" interchangeable therewith refers to a system, in which ribosomes are able to synthesize polypeptides even within mRNA in a eukaryotic cell, thus enabling the synthesis of multiple proteins from a single mRNA. In one embodiment of the present disclosure, the gene construct was designed to express the nucleic acid sequence of the MHC allele and the nucleic acid sequence encoding the tumor antigen at the same time from a single mRNA.

In general, prokaryotic cells have a polycistronic system capable of synthesizing several proteins at once by binding ribosomes at multiple sites of a single mRNA, whereas eukaryote cells, in principle, have a monocistronic system that synthesizes a single polypeptide by producing one mRNA from one promoter and translating only the gene. However, the gene construct of the present disclosure is able to express several polypeptides from a single mRNA in eukaryote cells, for example, it is able to express each gene by positioning the gene after each promoter, or to simultaneously express both genes under one promoter by placing an internal ribosome entry site (IRES) between the two genes.

As used herein, "comprising (the specified components)" may mean that it may include additional components other than the listed components ("comprising"), or it may essentially include the listed components ("consisting essentially of"). The term "major histocompatibility complex (MHC)" is a protein that presents antigen fragments to immune cells to discriminate between self and non-self molecules. There are two kinds of MHC class I and MHC class II. MHC class I is found in all nucleated cells, whereas MHC class II is found in antigen-presenting cells. The technical spirit provided herein is applicable to both MHC class I and MHC class II.

Generally, in the adaptive immune response, when pathogens or antigens enter the body, the antigen-presenting cells ingest them and breaks them down into short peptide fragments. The peptides bind to the MHC class I or MHC class II molecules within the cells to be transported to the cell surface. As described, when the peptides of pathogens or antigens bind to MHC class I or MHC class II to be presented on the cell surface of antigen-presenting cells, T cells recognize them through T cell receptors (TCRs) and are activated to initiate immune responses. In this respect, the peptides of pathogens or antigens correspond to the "epitope" of T cells.

Human MHC is called human leukocyte antigen (HLA), and MHC class I (or HLA class I) molecule comprises HLA-A, HLA-B, and HLA-C. MHC class I molecule consists of an alpha polypeptide chain and beta-2-microglobulin. MHC class I molecules interact with CD8+ cytotoxic T cells and play an important role in organ transplantation rejection or destruction of infected cells.

MHC class II (or HLA class II) molecule comprises HLA-DR, HLA-DQ, and HLA-DP. MHC class II molecule consists of an alpha polypeptide chain and a beta polypeptide chain. MHC class II molecules play an important role in inducing cellular immunity by recognizing non-self antigens through interaction with CD4+ helper T cells.

A gene encoding MHC is a gene with high polymorphism, and there are many different alleles to induce immune responses to various pathogens or antigens. For example, as of January 2020, the number of HLA class I alleles has been reported to be 18,000 or more and the number of HLA class II alleles has been reported to be 7,000 or more in humans. According to individual genetic loci, 5,735 HLA-A, 7,053 HLA-B, 5,653 HLA-C, 2,676 HLA-DRB1, 771 HLA-DQB11, 1,519 HLA-DPB1, etc. were reported (ebi.ac.uk/imgt/hla/). Relatively frequent alleles may be exemplified by HLA-A*2402, HLA-A*3303, HLA-A*0201, HLA-A*1101, HLA-A*0206, HLA-A*3101, HLA-A*0207, HLA-A*2601, HLA-A*2602, HLA-A*3001, HLA-A*0101, HLA-A*3004, HLA-A*0203, HLA-A*0301, HLA-A*0205, HLA-A*0215N, HLA-A*2408, HLA-A*2420, HLA-A*2610, HLA-A*2901, HLA-A*2603, HLA-A*3201, HLA-B*5101, HLA-B*1501, HLA-B*4403, HLA-B*3501, HLA-B*5801, HLA-B*4601, HLA-B*5401, HLA-B*1302, HLA-B*2705, HLA-B*0702, HLA-B*4006, HLA-B*4801, HLA-B*4001, HLA-B*5502, HLA-B*1301, HLA-B*4002, HLA-B*5201, HLA-B*5901, HLA-B*1401, HLA-B*3901, HLA-B*6701, HLA-B*0801, HLA-B*1507, HLA-B*1518, HLA-B*3701, HLA-B*3802, HLA-B*0705, HLA-B*1538, HLA-B*3511, HLA-B*4003, HLA-B*4402, HLA-B*5001, HLA-B*5102, HLA-B*5601, HLA-B*1502, HLA-B*1511, HLA-B*1527, HLA-B*3503, HLA-B*4701, HLA-B*5605, HLA-B*570, HLA-Cw*0102, HLA-Cw*0304, HLA-Cw*1402, HLA-Cw*0702, HLA-Cw*0801, HLA-Cw*0401, HLA-Cw*0302, HLA-Cw*0303, HLA-Cw*1403, HLA-Cw*0602, HLA-Cw*0701, HLA-Cw*1202, HLA-Cw*0802, HLA-Cw*0202, HLA-Cw*0704, HLA-Cw*1203, HLA- Cw*0501, HLA-Cw*1505, HLA-Cw*0103, HLA-Cw*1502, HLA-Cw*1507, etc., but the present disclosure is not limited thereto. Further, since HLA genes are located close to each other spanning 4 megabases on the short arm of chromosome 6, they have a characteristic that a child inherits one haplotype from each parent.

In one preferred embodiment, the MHC allele may be MHC class I allele or MHC class II allele.

In one preferred embodiment, the MHC allele may be derived from a target patient's tumor.

In one preferred embodiment, the gene construct comprises a nucleic acid sequence of the MHC allele and a nucleic acid sequence of the tumor antigen.

Further, the nucleic acid sequence encoding the MHC allele may be fused with a sequence encoding beta-2-microglobulin (B2M) at the N-terminus thereof, which may contribute to structural stability on the cell surface when the MHC allele is expressed in the antigen-presenting cells. B2M is a non-glycosylated protein of about 12 kDa that acts to stabilize MHC, particularly, the alpha polypeptide chain of MHC class I. The human B2M gene encodes a protein of 119 amino acids with 20 N-terminal amino acids encoding a leader sequence. A mature protein contains 99 amino acids. The gene comprises 4 exons and 3 introns, wherein exon 1 comprises the 5' untranslated region, the entire leader sequence, and first two amino acids of the mature peptide; exon 2 encodes the majority of the mature protein; exon 3 encodes the final four amino acids of the mature protein and a stop codon; and exon 4 contains the 3' non-translational region. Herein, stability of the peptide on the MHC molecule may be increased by fusion with B2M, and structural stability on the cell surface may be increased when expressed in antigen-presenting cells.

The sequence encoding B2M may comprise all or part of a nucleic acid residue corresponding to the whole human beta-2-microglobulin gene.

The term "tumor antigen" or "cancer antigen", which is an antigen expressed in a tumor (cancer), refers to a molecule that triggers an immune response. This immune response may involve antibody production or activation of specific immunologically-competent cells, or both of them.

The tumor antigen may be derived from a tumor-bearing organism, killed or inactivated whole tumor cells, or a lysate, and comprises any antigen derived from a tumor. The lysate refers to a substance resulting from the application of a process that causes disruption of the normal structure of cells. In addition, the tumor antigen comprises any protein or other material having antigenic properties, which is contained in tumor cells and expressed differently from normal cells.

For example, the tumor antigen comprises a tumor-associated antigen (TAA) and a tumor-specific antigen (TSA).

The tumor-associated antigen (TAA), which is an antigen expressed at higher levels in cancer cells than in normal cells or expressed in a different stage of differentiation from normal cells, is a tumor shared antigen also present at low levels in normal cells. Therefore, the immune response using TAA is highly likely to be hampered by self-tolerance, which is an immunosuppressive mechanism to prevent damage to own cells, or conversely, to attack unwanted organs due to autoimmunity.

Examples of the tumor-associated antigen (TAA) may comprise gp100, Melan-A/MART, MAGE-A, melanoma antigen E (MAGE), MAGE-3, MAGE-4, MAGE-A3, tyrosinase, TRP2, NY-ESO-1, carcinoembryonic antigen (CEA), PSA, p53, mammaglobin-A, survivin, Muc1 (mucin1)/DF3, metallopanstimulin-1 (MPS-1), cytochrome P450 isoform 1B1, 90K/Mac-2 binding protein, Ep-CAM (MK-1), HSP-70, hTERT (TRT), LEA, LAGE-1/CAMEL, TAGE-1, GAGE, 5T4, gp70, SCP-1, c-myc, cyclin B1, MDM2, p62, Koc, IMP1, RCAS1, TA90, OA1, CT-7, HOM-MEL-40/SSX-2, SSX-1, SSX-4, HOM-TES-14/SCP-1, HOM-TES-85, HDAC5, MBD2, TRIP4, NY-CO-45, KNSL6, HIP1R, Seb4D, KIAA1416, IMP1, 90K/Mac-2 binding protein, MDM2, NY-ESO-1, or LMNA, but are not limited thereto.

The tumor-specific antigen (TSA) refers to an antigen specifically present only in cancer cells. Particularly, when a tumor grows in a cancer patient, a cancer cell-specific gene mutation occurs and a new antigen epitope stimulating T cells is created, which is called neoantigen. In other words, a neoantigen contains a cancer cell-specific gene mutation, and is selectively expressed only in cancer cells, unlike the tumor-shared antigen, which is expressed at low levels even in normal cells. Thus, the neoantigen is recognized as a non-self foreign epitope by the own immune system and induces strong anticancer immune activity.

When a peptide produced from a mutated DNA is displayed on the MHC I on the cell surface, the T-cell receptor (TCR) recognizes the peptide. Since mutations do not occur in normal cells or tissues, neoantigen-specific T cells are free from self-tolerance or autoimmunity problems. Because of these advantages, neoantigens are considered as ideal targets for T-cell-based cancer immunotherapy.

The neoantigens are caused by a frame-shift deletion or insertion, in which one or more of nucleotides constituting DNA are added or deleted, leading to shifting the reading frame of codons, a point mutation resulting from the substitution of one nucleotide for another, other splice-site mutation, read-through mutation, or gene fusion mutation, etc., but are not limited thereto.

Neoantigens are predicted by specific cancer cell genome analysis of individual cancer patients. For example, cancer cells are obtained from a patient's tumor, and DNA is extracted therefrom, followed by sequencing analysis. The sequence is compared with a nucleic acid sequence of normal cells to select the part where the mutation has occurred. Then, among the nucleic acid sequences of several mutations, a neoantigen stimulating T cells may be identified. In this regard, processing of big data such as next gene sequencing (NGS), whole-exome sequencing (WES), or RNA sequencing, MHC binding prediction computer program, or artificial intelligence (AI) for neoantigen prediction may be used, but is not limited thereto. Because mutations are not shared between patients, neoantigens may be produced to personalized anticancer vaccines (personalized cancer vaccines).

The term "loading or pulsing" means that antigen-presenting cells (APCs) such as dendritic cells capture and degrade antigens, and display the antigens on the surface by loading them onto MHC molecules. As described, antigen-loaded cells may induce strong antigen-specific T lymphocyte activity.

The gene construct may comprise transcriptional and translational expression control sequences that allow the gene to be expressed in a selected host. The expression control sequence may comprise a promoter for performing transcription, a random operator sequence for controlling such transcription, and/or a sequence for controlling the termination of transcription and translation. Start codons and stop codons are generally considered as part of a nucleic acid sequence that encodes a target protein. It is necessary that they are functional in an individual to whom the gene construct is administered. The start codons and stop codons must be in frame with the coding sequence.

For example, the gene construct may comprise (a) a promoter, 5'-UTR, the nucleic acid sequence of the MHC allele, a nucleic acid sequence of an internal ribosome entry site (IRES), the nucleic acid sequence encoding the tumor antigen, and 3'-UTR in the 5' to 3' direction, or (b) a promoter, 5'-UTR, the nucleic acid sequence encoding the tumor antigen, the nucleic acid sequence of an internal ribosome entry site (IRES), the nucleic acid sequence of the MHC allele, and 3'-UTR in the 5' to 3' direction.

The term "promoter" refers to a DNA sequence site to which transcriptional regulators bind. With respect to the objects of the present invention, a promoter capable of inducing strong and stable gene expression may be used to increase a gene expression rate.

The promoter may be constitutive or inducible. The promoter may be exemplified by, but is not limited to, adenovirus early and late promoters, simian virus 40 (SV40), mouse mammary tumor virus (MMTV) promoter, HIV long terminal repeat (LTR) promoter, Moloney virus, cytomegalovirus (CMV) promoter, Epstein Barr virus (EBV) promoter, Rous sarcoma virus (RSV) promoter, RNA polymerase±promoter, T3 and T7 promoters, major operator and promoter regions of phage lambda, etc.

The term "5'-UTR" or "5'-untranslated region" refers to a region present at the 5'-terminus of an mRNA transcript but not translated into amino acids. In genomic sequences, 5'-UTR is generally defined as the region between the transcription start site and the start codon. 5'-UTR of vertebrate mRNA may vary from a few tens of bases up to several hundred bases in length. The translation of mRNA into protein starts with the binding of 30S ribosomal subunit to the 5'-UTR. Specifically, when 16S ribosomal RNA (16S rRNA) in the 30S ribosomal subunit binds to the ribosome binding site (RBS) of 5'-UTR, and tRNA recognizes and binds to the start codon (AUG) of mRNA, translation into protein starts. The ribosome binding site of 5'-UTR and the start codon are positioned approximately 6 to 8 nucleotides apart, and a sequence complementary to the 3'-end of 16S rRNA exists in the ribosome binding site, which is called Shine-Dalgarno sequence.

The term "IRES" or "internal ribosome entry site" refers to a nucleic acid sequence recognized by the ribosome as the start of the translation process during translation of the transcript. In other words, IRES is a specific region within mRNA to which ribosomes directly bind to enable synthesis of multiple polypeptides from a single mRNA in eukaryotic cells, and serves to enable the gene construct of the present disclosure to be bicistronic. That is, during translation, the polypeptide coding sequence located on the 5' part of the IRES is translated from the cap structure at the 5'-end, and the polypeptide coding sequence located on the other side of the IRES is translated by binding the ribosome subunits to the IRES. Therefore, several polypeptides may be obtained separately.

The IRES may be obtained naturally or synthetically, and may be derived from a virus such as poliovirus, EMC virus, etc., or may be derived from a cell, such as an immunoglobulin heavy chain binding protein (BiP) or an Antennapedia gene (Antp) of *Drosophila*, etc., but is not limited thereto.

The term "3'-UTR" or "3'-untranslated region" refers to a region present at the 3'-terminus of an mRNA transcript but not translated into amino acids.

In addition, the gene construct may appropriately comprise an adapter or a linker, an enhancer, a selectable marker (e.g., antibiotic resistance marker), a replication unit, a polyA sequence, a tag for purification (e.g., GST, poly-Arg, FLAG, histidine-tag (His-tag) or c-my, etc.) or other sequences of construction and induction known to regulate gene expression of prokaryotic or eukaryotic cells or viruses thereof and various combinations thereof, etc.

Further, the present disclosure relates to an RNA transcript transcribed from the above-described gene construct, the RNA transcript co-expressing the MHC allele and the tumor antigen. In terms of simultaneously translating and synthesizing the MHC allele and the tumor antigen from the RNA transcript, the RNA transcript is bicistronic.

The RNA transcript may be an mRNA transcript, and may be isolated and purified after being transcribed from the above-described gene construct in cells, and preferably, it may be transcribed in vitro by an in-vitro transcription method.

Further, the present disclosure relates to a bicistronic expression vector comprising the gene construct. The term "vector" refers to a gene construct comprising essential regulatory factors operably linked to express a gene insert encoding a target protein in an individual's cells, and various types of vectors such as plasmids, viral vectors, bacteriophage vectors, cosmid vectors, etc. may be used.

Description of each component of the expression vector and the RNA transcript is replaced with the description of each component of the above-described gene construct.

Another embodiment relates to a polypeptide produced from the gene construct, the expression vector comprising the gene construct, or the RNA transcript transcribed from the gene construct.

Still another embodiment relates to a composition for co-expressing the MHC allele and the tumor antigen gene, the composition comprising the above-described gene construct; the expression vector comprising the gene construct; the RNA transcript transcribed from the gene construct; or the polypeptide produced from the gene construct, expression vector, or RNA transcript.

Further, still another embodiment relates to antigen-presenting cells comprising the gene construct; the expression vector comprising the gene construct; the RNA transcript transcribed from the gene construct; or the polypeptide produced from the gene construct, expression vector, or RNA transcript.

Further, still another embodiment relates to a method of preparing a vaccine composition for preventing or treating cancer, the method comprising the step of introducing, into antigen-presenting cells, the gene construct, the expression vector comprising the gene construct, the RNA transcript transcribed from the gene construct; or the polypeptide produced from the gene construct, expression vector, or RNA transcript.

The term "antigen-presenting cell" refers to any cell that achieves the objects of the present disclosure by promoting enhancement of an immune response to an antigen (e.g., a tumor antigen). The antigen-presenting cells comprise dendritic cells (DCs), macrophages, or B cells. The antigen-presenting cell may be autologous (from a cancer patient) or allogeneic. The term "autologous" refers to cells obtained from an individual and used to treat the same individual, and the term "allogeneic" refers to cells obtained from another individual of the same species.

Dendritic cells (DC) are the most potent type of antigen-presenting cells in the body, and capable of phagocytosing foreign antigens and presenting them to naive (CD4+ or CD8+T) and memory T cells. Dendritic cells generally take up antigens by micropinocytosis and/or phagocytosis, followed by intracellular processing of these antigens, and presentation of the antigens to T cells of the immune system.

This processing usually occurs within the body. Alternatively, after isolating dendritic cells from the body, culturing the dendritic cells in vitro, and providing antigens to the dendritic cells in vitro cultured, the cells are allowed to interact with T cells. It is possible to return the cells to the body which can provoke an increased immune response to the antigen of interest. The process of providing the antigen to dendritic cells is commonly referred to as loading or pulsing or co-culturing.

In a specific embodiment, precursor cells of dendritic cells are obtained from a target patient or an individual of the same or different species, differentiated into dendritic cells, and then the above-described gene construct, RNA transcript, expression vector, or polypeptide may be introduced thereto. For example, dendritic cells may be obtained by differentiation of monocytes isolated from the blood of a patient to be administered with a vaccine. Techniques for the differentiation of dendritic cells from monocytes are well established in the art. As a non-limiting example, in a classic protocol, peripheral blood mononuclear cells (PBMCs) may be isolated from the whole blood by density gradient centrifugation, and isolating of monocytes from PBMCs may be performed by using the adherence of monocytes or immunomagnetic beads. The isolated monocytes may be cultured in the presence of GM-CSF and IL-4 to differentiate into immature dendritic cells. Immature dendritic cells may be cultured in the presence of a maturation factor, typically, a TLR-4 agonist, such as LPS, or cultured and matured using a monocyte maturation cocktail containing TNFα, IL-6, IL-1β, and PGE2. Maturation of dendritic cells and introduction of vector may be performed at the same time.

Introduction of the gene construct, RNA transcript, or expression vector into cells may be performed by using an appropriate standard techniques as known in the art, for example, electroporation, electroinjection, microinjection, calcium phosphate co-precipitation, a calcium chloride/rubidium chloride method, retroviral infection, DEAE-dextran, a cationic liposome method, polyethylene glycol-mediated uptake, gene guns, etc., but is not limited thereto. At this time, the vector may be introduced in a linearized form by digestion of a circular construct with appropriate restriction enzymes.

In a preferred embodiment, the gene construct, RNA transcript, expression vector, or polypeptide may be introduced by electroporation. Electroporation refers to application of an electric current or an electric field to cells to facilitate the entry of an impermeable material into the cells. For example, when cells are suspended in a solution containing an impermeable substance to be introduced (e.g., nucleic acid, vector, etc.) and a pulse of DC high voltage is passed through it, holes are made in the cell membrane by electricity, and at the same time, the impermeable substance may be introduced into the cells by the action of electrophoresis. An electroporation device may be a static-type electroporation device or a flow-type electroporation device. The static-type electroporation device comprises a specialized cuvette containing molded-in electrodes in fluid contact with a fixed volume of target cells. Molecules of interest are placed between two electrodes and pulsed with high voltage.

Still another embodiment relates to a vaccine composition for preventing or treating cancer, the vaccine composition comprising the above-described gene construct, RNA transcript, expression vector, or polypeptide, and a preparation method thereof.

Still another embodiment relates to a vaccine composition for preventing or treating cancer, the vaccine composition comprising antigen-presenting cells into which the above-described gene construct, RNA transcript, expression vector, or polypeptide is introduced, and a preparation method thereof.

Still another embodiment relates to a vaccine composition for preventing or treating cancer, the vaccine composition comprising antigen-presenting cells, on the cell surface of which the complex of the MHC allele and the tumor antigen is overexpressed, and a preparation method thereof.

The term "vaccine" refers to a formulation comprising the antigen-presenting cells according to the present disclosure, which may be administered to a subject. Therefore, the vaccine composition of the present invention may be conveniently used to prevent, improve, or treat diseases. After being introduced into a subject or host, the vaccine is able to elicit an immune response comprising, but not limited to, production of antibodies, cytokines, and/or other cellular responses.

In a preferred embodiment, the MHC allele and the tumor antigen may be derived from tumor cells of a target cancer patient to be administered with the composition.

The cancer vaccine composition of the present disclosure may overexpress the tumor antigen sequence obtained from the patient tumor analysis, particularly, the neoantigen sequence and the MHC allele derived from each patient's tumor at the same time in antigen-presenting cells (APCs), thereby expressing the maximum amount of antigen (or epitope)-MHC immunostimulatory complex on the cell surface to maximize the tumor antigen presentation efficacy of APCs. Ultimately, the cancer vaccine composition may stimulate the proliferation and activation of patient-specific anti-cancer T cells as much as possible, thereby enhancing the anti-cancer immune effect.

Specifically, the antigen-presenting cells (e.g., dendritic cells) comprised in the cancer vaccine composition of the present disclosure may overexpress the MHC allele and the tumor antigen at the same time, whereby the MHC allele and the tumor antigen combine with each other to be expressed on the surface of the antigen-presenting cells, and the antigens may be presented to T lymphocytes. At a result, when T lymphocytes are activated, strong cancer-specific cytotoxic T lymphocytes (CTLs) are induced, destroying cancer cells, thereby immunologically treating cancer. In addition, costimulatory substances abundantly expressed on antigen-presenting cells (e.g., dendritic cells) play an important role in the reaction between T lymphocyte receptors and antigen-MHC complexes, and secrete several cytokines involved in T lymphocyte differentiation, growth, or influx to regulate the activity of the immune response. Thus, the vaccine composition may be usefully applied to anticancer immunotherapy.

The vaccine composition of the present disclosure may comprise additional adjuvant to enhance effectiveness of the vaccine. Appropriate adjuvants comprise (1) aluminum salts (alum), for example, aluminum hydroxide, aluminum phosphate, aluminum sulfate, etc.; (2) oil-in-water emulsion formulations (with or without other specific immunostimulating agents such as muramyl peptides or bacterial cell wall components), for example, (a) MF5 (WO90/14837) containing 5% Squalene, 0.5% Tween 80, and 0.5% Span 85 (optionally, containing various amounts of N-acetylmuramyl-L-alanyl-D-isoglutaminyl-L-alanine-2-(1'-2'-dipalmitoyl-sn-glycero-3-hyd roxyphosphoryloxy)-ethylamine (MTP-FE)) formulated into submicron particles, (b) SAF containing 10% Squalene, 0.4% Tween 80, 5% pluronic-blocked polymer, and N-acetylmuramyl-L-threonyl-D-isoglutamine (thr-MDP) either microfluidized into a submicron particles or vortexed to generate a larger particle size emulsion, and (c) Ribi™ adjuvant system (RAS) containing one or more bacterial cell wall components selected from the group consisting of monophosphorylipid A (MPL), trehalose dimycolate (TDM), and cell wall skeleton (CWS), 2% Squalene, and 0.2% Tween 80; (3) saponin adjuvants; (4) Complete Freund's Adjuvant (CFA) and Incomplete Freund's Adjuvant (IFA); (5) cytokines, for example, interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc.; (6) bacterial ADP-ribosyltransferase toxins, for example, cholera toxin (CT), pertussis toxin (PT), or *E. coli* heat-labile toxin (LT), particularly, detoxified mutants of LT-R72, CT-S109, PT-K9/G129 (WO93/13302 and WO92/19265); and (7) other materials acting as adjuvants to enhance effectiveness of vaccines, but are not limited thereto.

The vaccine composition may comprise a common saline or buffered aqueous solution medium, suspended or dissolved. For example, it may commonly comprise a diluent, e.g., water, saline, glycerol, ethanol, etc. Auxiliary substances, e.g., wetting agents, emulsifiers, pH buffering agents, etc. may be present in the composition.

Formulations suitable for injection comprise sterile aqueous solutions (water soluble) or dispersions and sterile powders for the extemporaneous preparation of sterile injectable solutions or dispersion. They must be stable under the conditions of manufacture and must be preserved against the contaminating action of microorganisms such as bacteria and fungi. Microbial contamination may be prevented by various antibacterial and antifungal agents, for example, parabens, chlorobutanol, phenol, ascorbic acid, thimerosal, etc. In many cases, it is preferable to comprise isotonic agents, for example, sugars or sodium chloride. Prolonged absorption of the injectable compositions are brought about by using, in the composition, an agent which delays absorption, e.g., aluminum monostearate or gelatin.

Sterile injectable solutions may be prepared by incorporating the required amount of the antigen-presenting cells in the above-described solvent with various other components listed above, as needed, followed by filtered sterilization of remaining components, except for antigen-presenting cells and/or heat-sensitive adjuvant cytokines, etc., for example, a buffer solution such as PBS. Generally, dispersions are prepared by incorporating various sterilized active components into a sterile vehicle which contains a basic dispersion medium and the required other ingredients from those described above. In the case of sterile powders for the preparation of sterile injectable solutions, preferred preparation methods are vacuum drying and freeze drying, which yields a powder of the active ingredient, and any additional desired ingredient from a previously sterile filtered solution thereof.

Without limiting the action of the present invention in any way, delivery of the dendritic cells according to the present invention is particularly useful for inducing immune responses, in particular for inducing responses of cytotoxic T-lymphocytes to antigens. The immune responses may be specific (T cell and/or B cell) and/or non-specific immune responses.

Accordingly, still another aspect of the present invention relates to a method of raising, inducing, or promoting immune responses to antigens in humans, particularly, cancer patients, the method comprising administering, to cancer patients, an effective amount of the above-described vaccine composition or antigen-presenting cells.

The immune responses preferably comprise cytotoxic T-lymphocyte responses, and the cytotoxic lymphocyte responses of the present invention may occur independently or together with helper T-cell responses, humoral responses, or other specific or non-specific immune responses.

Still another aspect of the present invention relates to use of the dendritic cells of the present invention in connection with the treatment and/or prevention of a disease state. Examples of the diseases that may be treated according to the method of the present invention comprise various cancer diseases and intractable cancer diseases.

The diseases may be, for example, solid cancer or blood cancer. Non-limiting examples thereof may comprise breast cancer, lung cancer, prostate cancer, ovarian cancer, brain cancer, liver cancer, cervical cancer, endometrial cancer, uterine cancer, colon cancer, colorectal cancer, colorectal cancer, rectal cancer, kidney cancer, nephroblastoma, skin cancer, oral squamous cell carcinoma, epidermal cancer, nasopharyngeal cancer, head and neck cancer, bone cancer, esophageal cancer, bladder cancer, lymphatic cancer (e.g., Hodgkin's lymphoma or non-Hodgkin's lymphoma), stomach cancer, pancreatic cancer, testicular cancer, thyroid cancer, follicular carcinoma, melanoma, myeloma, multiple myeloma, mesothelioma, osteosarcoma, myelodysplastic syndrome, tumor of mesenchymal origin, soft tissue sarcoma, liposarcoma, gastrointestinal stromal tumor, malignant peripheral nerve sheath tumor (MPNST), Ewing's sarcoma, leiomyosarcoma, mesenchymal chondrosarcoma, lymphosarcoma, fibrosarcoma, rhabdomyosarcoma, teratoma, neuroblastoma, medulloblastoma, glioma, benign skin tumor, or leukemia. The lung cancer may be, for example, small cell lung carcinoma (SCLC) or non-small cell lung carcinoma (NSCLC). The leukemia may be, for example, acute myeloid leukemia (AML), chronic myelogenous leukemia (CML), acute lymphocytic leukemia (ALL) or chronic lymphocytic leukemia (CLL). The subject to be treated may be a subject receiving a second-line anti-hyperproliferative therapy. For example, the second-line anti-hyperproliferative therapy may be chemotherapy, radiation therapy, immunotherapy, phototherapy, cryotherapy, toxin therapy, hormone therapy, or surgery.

Accordingly, still another aspect of the present invention provides a method of treating cancer by enhancing tumor-specific immune responses using the cancer vaccine composition. Here, administration of the composition causes, induces, or otherwise promotes immune responses that inhibit, stop, delay, or prevent the onset or progression of a disease state.

Direct delivery of the composition may be generally systemic, subcutaneous, intradermal, intraperitoneal, intravascular (intravenous), intramuscular, or local delivery, or delivered through interstitial tissue. The composition may also be administered to a lesion. Dosage regimen may be a single dose or multiple dose schedule.

The term "effective amount" refers to an amount sufficient to achieve a desired result, for example, an amount effective to treat or prevent cancer, when administered to an individual, comprising a human. The effective amount may vary depending on factors such as the individual's disease state, age, sex, body weight, etc. Dosage or therapeutic regimen may be adjusted to provide an optimal therapeutic response as will be understood by those skilled in the art.

A therapeutic regimen for an individual with a therapeutically effective amount may consist of a single administration, or in other instances, may comprise a series of applications. The period of the treatment depends on various factors, such as severity of the disease, the individual's age, the concentration of the cancer vaccine, the patient's responsiveness to the cancer vaccine, or a combination thereof. It will also be appreciated that the effective dosage of the cancer vaccine used for treatment may be raised or lowered over the course of an individual therapeutic regimen. Variations in dosage may occur and will be apparent through standard diagnostic assays known in the art. The cancer vaccine of the present invention, in some aspects, may be administered before, during, or after treatment using common anticancer agents, radiation therapy, hormone therapy, biotherapy and/or surgical tumor resection.

Detailed Description of the Embodiments

Hereinafter, the present invention will be described in more detail with reference to the following exemplary embodiments. However, these are only for illustrating the present invention, and the scope of the present invention is not limited by these exemplary embodiments.

Example 1. Preparation of Bicistronic Expression Vector

A bicistronic vector for co-expressing an MHC class I allele and a tumor antigen has a configuration as in FIG. 1, and specifically, the bicistronic vector comprises a gene construct comprising, in the 5' to 3' direction, 5'UTR-ORF1 (open reading frame comprising a fusion of recombinant B2M and MHC class I allele; in detail, a coding sequence of a fusion protein comprising B2M at the N-terminus and tumor-derived MHC class I allele at the C-terminus)-IRES-ORF2 (a coding sequence of recombinant protein consisting of polyantigen epitope as beads-on-a-string format)-3'UTR. Specifically, a reference template is named "LGV1007", and has a coding sequence of a fusion protein (SEQ ID NO: 1) comprising a signal sequence, B2M, and HLA-A*0201 in the N-terminus to the C-terminus direction as ORF1, and a coding sequence of a shared antigen recombinant protein (SEQ ID NO: 2) comprising NY-ESO1, MAGE-A3, SURVIVIN, MULTI-MAGE-A, and MELAN-A as ORF2. The entire sequence structure of the LGV1007 is as shown in FIG. 2, and the entire DNA sequence (3,523 bp) comprising the site from BamHI at the 5' end to XbaI restriction enzyme at the 3' end of the LGV1007 is shown in SEQ ID NO: 3, and gene synthesis thereof was requested and provided (GeneArt, Thermo Fisher). However, LGV1007 is only a representative example according to one embodiment of the present disclosure, and the nucleic acid sequences of ORF1 and ORF2 may be changed to comprise autologous sequences customized for individual cancer patients as described above, and nucleic acid sequences except for ORF1 and ORF2 may be optimized and standardized for antigen presentation using sequences widely known in the art.

Example 2. Production of mRNA Transcript Using In-Vitro Transcription (IVT)

In order to generate a bicistronic mRNA transcript, the bicistronic vector (DNA plasmid vector) obtained in Example 1 was linearized by digestion using a restriction enzyme XbaI, and the linearized DNA was purified by using Expin™ combo GP kit (GeneAll, 112-102). The purified linearized plasmid template was used in mRNA production by in-vitro transcription (IVT) using a mMessage mMachine™ T7 Ultra transcription kit (ThermoFisher) according to the manufacturer's instructions. The resulting mRNA transcripts were finally purified using a LiCl precipitation method. In detail, mRNA products were mixed lightly with a LiCl precipitation solution (50 μL per 20 μL of IVT reaction) and incubated at −20° C. for 30 min or more. Next, the samples were spun down by centrifugation at 20,000×g for 14 minutes at 4° C. The pellet was then washed with 70% ethanol. The final mRNA product was resuspended in deionized water without nuclease. The amount of mRNA product was measured using Nanodrop2000.

FIG. 3 shows PAGE electrophoresis results of examining production of the mRNA transcript resulting from in-vitro transcription of the reference template LGV1007. The expected correct size of the product (~3.5 Kb, lane 1) was confirmed.

Example 3. Cell Electroporation for Intracellular mRNA Transfection

The mRNA transcript obtained in 2 above was transferred to human cells using cell electroporation. K562 human bone marrow-derived lymphoblastic leukemia cells (ATCC CCL-243™) were electroporated using an Amaxa™ 4D-Nucleofector™ X Unit device and SF Cell Line Nucleofector™ Solution (Lonza) according to the manufacturer's protocol. K562 cells were freshly isolated at $3\times10^5$ cells/ml two days before electroporation. On the day of electroporation, cells were counted and the required number of cells ($1\sim2\times10^6$ cells) was prepared at room temperature. Prior to electroporation, cells were washed twice with serum-free RPMI or Opti-MEM (Gibco) and finally resuspended in 100 μl of SF Cell Line 4D Nucleofector™ X Solution (82 μl of nucleofection solution, 18 μl of supplement). Then, 0.1 ml of the cell suspension was mixed with 0 μg to 20 μg of in-vitro transcribed (IVT) LGV1007 mRNA using the program FF-120. After electroporation, a fresh culture medium was added to the cell suspension, and the electroporated cells were directly incubated at 37° C. in a $CO_2$ cell culture incubator.

FIG. 4 shows results of examining expression levels of HLA-A*0201 molecules for 9 days after electroporation of K562 cells with the LGV1007 mRNA transcript in an amount of 0 μg, 3 μg, 5 μg, or 10 μg per $1\times10^6$ cells in order to derive conditions under which the expression levels reach the maximum level after electroporation of K562 cells with the LGV1007 mRNA transcript. 24 hours after electroporation of 10 μg of the transcript, the maximum expression level (up to ~65 folds the reference expression level) was observed, and after 48 hours, it sharply decreased and was continuously maintained at the expression level of 5 folds to 2 folds the reference value. The maximal overexpression of MHC-I allele of the non-antigen-presenting cell (i.e., personalized for tumors of individual patients) has the effect of customizing the MHC-I phenotype of a specific antigen-presenting cell for the patient tumor, and thus it is expected to maximize the activation of the individual patient's anti-cancer immune T cells.

Example 4. In-Vitro Translation of mRNA Product

For in-vitro translation of the Flag-tagged polyantigen recombinant protein, the LGV1007 template DNA plasmid was used in single tube in-vitro transcription/in-vitro translation using a TnT Quick Coupled Transcription/Translation kit (Promega) or a 1-Step Human High-Yield Mini IVT kit (Thermo Scientific) according to the manufacturer's manual. The reaction volume was scaled down from 100 μl to 25 μl. In the case of the TnT Quick Coupled Transcription/Translation kit (Promega), the reaction mixture was incubated at 30° C. for 60 minutes to 90 minutes, and in the case of the 1-Step Human High-Yield Mini IVT kit (Thermo Scientific), the reaction time was 6 hours to 16 hours.

FIG. 5 shows results of Western blotting for confirming production of the Flag-tagged polyantigen recombinant protein after in-vitro translation of the LGV1007 mRNA transcript.

Example 5. Protein Expression Analysis

After electroporation of mRNA into K562 cells, Western blot analysis was performed on cell expression of the recombinant MHC-I protein in which B2M and HLA-A*0201 were fused. In addition, Western blotting of the in-vitro translated flag-tagged polyantigen recombinant protein was performed to confirm the protein expression of the polyantigen recombinant protein. In detail, K562 cells electroporated with LGV1007 mRNA were collected, washed twice with PBS, and lysed in a RIPA lysis buffer (ATTO) containing a protease inhibitor cocktail (ATTO) at 4° C. According to a standard Western blot protocol, 20 μg~30 μg of the protein was mixed with an SDS sample buffer, and analyzed by running SDS-PAGE on a Tris-Glycine precast 12% or 4%-20% gel (KOMABIOTECH). Immunoblot antibodies were obtained from the following sources: beta-2 microglobulin (Cell Signaling) and FLAG (Sigma-Aldrich). Anti-beta-2 microglobulin antibody or anti-FLAG M2 antibody was applied overnight at 4° C. Horseradish peroxidase (HRP)-conjugated secondary antibodies (Santa Cruz Biotechnology) were applied at room temperature for 1 hour. Immunoreactive proteins were identified using an enhanced chemoluminescence detection kit (ECL, Amersham or Pierce). Signals from Western blotting were detected using Amersham Imager 680.

FIG. 6 shows results of Western blotting for confirming protein expression of both MHC class I allele (ORF1) and tumor antigen (ORF2) after electroporation of K562 cells with the LGV1007 mRNA transcript, confirming that ORF1 (B2M-HLA-A*0201) protein had a size of ~51 kDa (FIG. 6A), and ORF2 (tumor antigen fusion protein) was expressed at the expected size of ~30 kDa (FIG. 6B). However, since the tumor antigen fusion protein is rapidly degraded by the proteasome upon cell expression, it was clearly expressed only by the in-vitro translation method.

Example 6. Flow Cytometry

Flow cytometry was performed using an Intellicyt iQue™ Screener PLUS (Sartorius) flow cytometer. In detail, 24 hours to 72 hours or up to 2 weeks after nucleofection, LGV series mRNA-electroporated K562 cells were collected and centrifuged at 300×g for 5 minutes. The cell pellet was resuspended in a flow cytometry buffer (DPBS containing 1% FBS and 2 mM EDTA). For cell staining, APC conjugated-mouse anti-human HLA-A2 (BD Pharmigen) was added at the recommended concentration, and then cells were stained by incubation for 30 minutes to 1 hour at room temperature in the dark. After staining incubation, the cells were pelleted and resuspended in PBS. Flow cytometry results were analyzed with an Intellicyt ForeCyt software (Sartorius).

FIG. 7 shows results of flow cytometry for confirming expression levels on the surface of K562 cells at 24 hours after electroporation of the K562 cells with the LGV1007 mRNA transcript in an amount of 1 μg per $1\times10^6$ cells. Excessive expression of ~10 folds or more compared to the reference value was observed.

Example 7. Immune Cell Activation Using ELISPOT IFNγ Cytokine Release Assay

In K562apc antigen-presenting cells, superiority of the immunological efficacy was compared between a traditional antigen loading method, peptide pulse, and RNA antigen loading. In detail, on day 1, K562apc cells electroporated with LGV1007 mRNA transcripts (five antigen sequences comprised: SURVIVIN, MARTI, NYESO1, MAGEA3, MULTIMAGE) prepared in Example 3, K562apc cells loaded with a reference antigen (SURVIVIN, peptide of 9 amino acids), or K562apc control cells untreated with the peptides were subjected to immune activity comparison by ELISPOT IFNγ assay. Purified PBMC (Peripheral blood mononuclear cell) CD8+ T cells in a cell suspension of APC 2.5×10e5 cells/ml were stimulated. 100 μL of T cells/well and 100 μL of APCs/well were added (T cells vs APC mixed at a ratio of 2:1 to 10:1) and the cell mixture was incubated at 37° C. for 24 hours. On day 2, the culture medium was replaced with 10 U/mL of IL-2 and 5 ng/ml of IL-15, and after 7 days, re-supplemented with IL-2. After 11 days of APC stimulation, IFNγ-releasing T cells were analyzed by ELISPOT IFNγ protocol (BD Bioscience) according to the manufacturer's instructions. Positive spot color development was carefully monitored and assay plates were air-dried at room temperature for 2 hours to overnight until complete dryness. PBMC T cell activation assay was performed by directly counting positive spots by observation with a dissecting microscope or by automatically counting positive spots using an ELISPOT plate reader.

FIG. 8 shows results of the ELISPOT IFNγ release assay for measuring the immune activity of PBMC T cells by K562apc cells electroporated with the LGV1007 mRNA transcript, K562apc cells loaded with the reference antigen (SURVIVIN, peptide of 9 amino acids), and K562apc control cells untreated with the peptides. The K562 antigen-presenting cells activated through electroporation with the reference RNA, LGV1007 primed and activated PBMC CD8+ T cells bearing the homologous MHC class I allele (HLA-A*0201), and thus the positive spots releasing IFNγ were observed. In contrast, CD8 T cells derived from heterologous MHC class I allele (non-HLA-A*0201) used as MHC genotype-restricted controls were not primed by APCs. Through this experiment, it was confirmed that K562apc cells electroporated with the LGV1007 mRNA transcript elicited superior activation of ex vivo human PBMC immune cells, as compared to traditional peptide antigen loading.

Example 8. Preparation of LGV1032-Introduced Autologous Dendritic Cells and Immune Cell Activation Using the Same An experiment was conducted to verify whether the LGV RNA antigen loading method effectively promotes antigen-specific immune cell activation through effective antigen loading and antigen presentation even in personalized autologous dendritic cells with various MHC class I and class II, which were extracted and cultured from each patient, as well as in K562apc technically optimized in the laboratory. The results are shown in FIGS. 9 and 10.

FIG. 9 shows an illustration of a configuration of the LGV1032 mRNA transcript and results of FACS analysis for confirming cell expression in individual-derived autologous dendritic cells. LGV1032 has a bicistronic transcript configuration homogeneous with that of LGV1007 (Example 1), maintains ORF2 (tumor antigen part), and has a GFP reporter protein as a cell expression marker positioned in ORF1. Therefore, the preparation method of LGV1032 is the same as that of LGV1007. As a result of flow cytometry as described above, it was confirmed that LGV1032, like LGV1007, was also effectively expressed in individual-derived autologous dendritic cells after being introduced into the cells by the electroporation method. The individual-derived or personalized autologous dendritic cells were obtained by collecting blood, differentiating monocytes into immature dendritic cells, and then obtaining mature dendritic cells through a maturation process. It is known that although this in-vitro cell differentiation and maturation process takes about a week, the final mature dendritic cells possess the maximum antigen-presenting ability. As shown in the results of FACS analysis of the GFP reporter protein in FIG. 9, it was confirmed that LGV1032 was effectively electroporated into cells of all stages (monocyte, immature DC, mature DC), and after introduced into the cells, they were expressed.

FIG. 10 shows results of confirming the increased spots in the ELISPOT IFNγ release assay, demonstrating that LGV1032 electroporated into individual-derived autologous dendritic cells (MoDCs) effectively promoted antigen-specific T cell immune activity. The increased spots in the ELISPOT IFNγ release assay clearly verified that the autologous dendritic cells electroporated with LGV1032 (FIG. 10, columns 3 & 4) quite effectively promotes MARTI antigen-specific TCRe T cell activation, as compared to autologous dendritic cells (FIG. 10, column 2) pulsed with the peptide antigen, which is a traditional method.

Based on the above description, it will be understood by those skilled in the art that the present disclosure may be implemented in a different specific form without changing the technical spirit or essential characteristics thereof. In this regard, it should be understood that the above exemplary embodiments are not limitative, but illustrative in all aspects. The scope of the present invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A vaccine composition for preventing or treating cancer, comprising antigen-presenting cells, wherein a complex of a major histocompatibility complex (MHC) and a tumor antigen is overexpressed on the cell surface of the antigen-presenting cells, wherein the antigen-presenting cells comprise:

a bicistronic gene construct co-expressing an allele of the MHC and the tumor antigen;

a bicistronic expression vector comprising a gene construct co-expressing the MHC allele and the tumor antigen; or a bicistronic RNA transcript co-expressing the MHC allele and the tumor antigen gene, which is transcribed from a gene construct co-expressing the MHC allele and the tumor antigen.

2. The vaccine composition of claim 1, wherein the antigen-presenting cells are dendritic cells, or autologous or allogeneic antigen-presenting cells of a cancer patient.

3. The vaccine composition of claim 1, wherein the MHC is MHC class I or MHC class II.

4. The vaccine composition of claim 1, wherein the bicistronic gene construct comprises a nucleic acid sequence of the MHC allele and a nucleic acid sequence encoding the tumor antigen, and the nucleic acid sequence of the MHC allele is optionally fused with a sequence encoding beta-2-microglobulin (B2M) at the N-terminus thereof.

5. The vaccine composition of claim 1, wherein the MHC allele and the tumor antigen are derived from tumor cells of a cancer patient to be treated.

6. The vaccine composition of claim 1, wherein the tumor antigen comprises a tumor-associated antigen (TAA);

a tumor-specific antigen (TSA); or a tumor-derived neoantigen or a mutation specifically expressed in cancer cells.

7. The vaccine composition of claim 6, wherein the tumor-associated antigen (TAA) is gp100, Melan-A/MART, MAGE-A, melanoma antigen E (MAGE), MAGE-3, MAGE-4, MAGE-A3, tyrosinase, TRP2, NY-ESO-1, carcinoembryonic antigen (CEA), PSA, p53, mammaglobin-A, survivin, Muc1 (mucin1)/DF3, metallopanstimulin-1 (MPS-1), cytochrome P450 isoform 1B1, 90K/Mac-2 binding protein, Ep-CAM (MK-1), HSP-70, hTERT (TRT), LEA, LAGE-1/CAMEL, TAGE-1, GAGE, 5T4, gp70, SCP-1, c-myc, cyclin B1, MDM2, p62, Koc, IMP1, RCAS1, TA90, OA1, CT-7, HOM-MEL-40/SSX-2, SSX-1, SSX-4, HOM-TES-14/SCP-1, HOM-TES-85, HDAC5, MBD2, TRIP4, NY-CO-45, KNSL6, HIP1R, Seb4D, KIAA1416, IMP1, 90K/Mac-2 binding protein, MDM2, NY-ESO-1, or LMNA.

8. The vaccine composition of claim 1, wherein the bicistronic gene construct comprises:

(a) a promoter, 5'-UTR, the nucleic acid sequence of the MHC allele, a nucleic acid sequence of an internal ribosome entry site (IRES), the nucleic acid sequence encoding the tumor antigen, and 3'-UTR in the 5' to 3' direction, or (b) a promoter, 5'-UTR, the nucleic acid sequence encoding the tumor antigen, the nucleic acid sequence of an internal ribosome entry site (IRES), the nucleic acid sequence of the MHC allele, and 3'-UTR in the 5' to 3' direction, wherein the nucleic acid sequence of the MHC allele is optionally fused with a sequence encoding beta-2-microglobulin (B2M) at the N-terminus thereof.

9. The vaccine composition of claim 1, wherein the bicistronic gene construct, the bicistronic expression vector, or the bicistronic RNA transcript, is introduced into antigen-presenting cells by electroporation.

10. A method of treating cancer, the method comprising the step of administering an antigen-presenting cells to a patient, wherein a complex of a major histocompatibility complex (MHC) and a tumor antigen is overexpressed on the cell surface of the antigen-presenting cells, wherein the antigen-presenting cells comprises:

a bicistronic gene construct co-expressing an allele of the MHC and the tumor antigen;

a bicistronic expression vector comprising a gene construct co-expressing the MHC allele and the tumor antigen; or a bicistronic RNA transcript co-expressing the MHC allele and the tumor antigen gene, which is transcribed from a gene construct co-expressing the MHC allele and the tumor antigen.

11. The method of claim 10, wherein the antigen-presenting cells are dendritic cells, or autologous or allogeneic antigen-presenting cells of a cancer patient.

12. The method of claim 10, wherein the MHC is MHC class I or MHC class II.

13. The method of claim 10, wherein the bicistronic gene construct comprises a nucleic acid sequence of the MHC allele and a nucleic acid sequence encoding the tumor antigen, and the nucleic acid sequence of the MHC allele is optionally fused with a sequence encoding beta-2-microglobulin (B2M) at the N-terminus thereof.

14. The method of claim 10, wherein the MHC allele and the tumor antigen are derived from tumor cells of a cancer patient to be treated.

15. The method of claim 10, wherein the tumor antigen comprises:

a tumor-associated antigen (TAA);

a tumor-specific antigen (TSA); or a tumor-derived neoantigen or a mutation specifically expressed in cancer cells.

16. The method of claim 15, wherein the tumor-associated antigen (TAA) is gp100, Melan-A/MART, MAGE-A, melanoma antigen E (MAGE), MAGE-3, MAGE-4, MAGE-A3, tyrosinase, TRP2, NY-ESO-1, carcinoembryonic antigen (CEA), PSA, p53, mammaglobin-A, survivin, Muc1 (mucin1)/DF3, metallopanstimulin-1 (MPS-1), cytochrome P450 isoform 1B1, 90K/Mac-2 binding protein, Ep-CAM (MK-1), HSP-70, hTERT (TRT), LEA, LAGE-1/CAMEL, TAGE-1, GAGE, 5T4, gp70, SCP-1, c-myc, cyclin B1, MDM2, p62, Koc, IMP1, RCAS1, TA90, OA1, CT-7, HOM-MEL-40/SSX-2, SSX-1, SSX-4, HOM-TES-14/SCP-1, HOM-TES-85, HDAC5, MBD2, TRIP4, NY-CO-45, KNSL6, HIP1R, Seb4D, KIAA1416, IMP1, 90K/Mac-2 binding protein, MDM2, NY-ESO-1, or LMNA.

17. The method of claim 10, wherein the bicistronic gene construct comprises:

(a) a promoter, 5'-UTR, the nucleic acid sequence of the MHC allele, a nucleic acid sequence of an internal ribosome entry site (IRES), the nucleic acid sequence encoding the tumor antigen, and 3'-UTR in the 5' to 3' direction, or (b) a promoter, 5'-UTR, the nucleic acid sequence encoding the tumor antigen, the nucleic acid sequence of an internal ribosome entry site (IRES), the nucleic acid sequence of the MHC allele, and 3'-UTR in the 5' to 3' direction, wherein the nucleic acid sequence of the MHC allele is optionally fused with a sequence encoding beta-2-microglobulin (B2M) at the N-terminus thereof.

18. The method of claim 10, wherein the bicistronic gene construct, the bicistronic expression vector, or the bicistronic RNA transcript is introduced into antigen-presenting cells by electroporation.

* * * * *